(12) United States Patent
Nakae et al.

(10) Patent No.: US 9,732,042 B2
(45) Date of Patent: Aug. 15, 2017

(54) METHOD FOR PRODUCING PYRIDAZINE COMPOUND

(71) Applicant: SUMITOMO CHEMICAL COMPANY, LIMITED, Tokyo (JP)

(72) Inventors: Yasuyuki Nakae, Takarazuka (JP); Takayuki Wakamatsu, Oita (JP); Takashi Miyamoto, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/892,266

(22) PCT Filed: Apr. 24, 2014

(86) PCT No.: PCT/JP2014/062122

§ 371 (c)(1),
(2) Date: Nov. 19, 2015

(87) PCT Pub. No.: WO2014/188863

PCT Pub. Date: Nov. 27, 2014

(65) Prior Publication Data

US 2016/0090363 A1 Mar. 31, 2016

(30) Foreign Application Priority Data

May 24, 2013 (JP) ................. 2013-109620

(51) Int. Cl.
  *C07D 237/12* (2006.01)
  *C07D 237/14* (2006.01)
  *C07D 237/18* (2006.01)

(52) U.S. Cl.
  CPC ......... *C07D 237/12* (2013.01); *C07D 237/14* (2013.01); *C07D 237/18* (2013.01)

(58) Field of Classification Search
  CPC .................................................. C07D 237/12
  See application file for complete search history.

(56) References Cited

U.S. PATENT DOCUMENTS

| 6,380,134 B1 | 4/2002 | Kunz et al. |
| 7,569,518 B2 | 8/2009 | Morishita et al. |

(Continued)

FOREIGN PATENT DOCUMENTS

| CN | 1301262 A | 6/2001 |
| CN | 1942449 A | 4/2007 |

(Continued)

OTHER PUBLICATIONS

Kweon et al., "Arenesulfonylheterocycles (I): Synthesis and Reactions of 2-Benzenesulfonyl-4,5 dichloropyridazin-3-ones with Amines," J. Heterocyclic Chem., vol. 39, Jan.-Feb. 2002, pp. 203-211.

(Continued)

*Primary Examiner* — Paul V Ward
(74) *Attorney, Agent, or Firm* — Birch, Stewart, Kolasch & Birch, LLP

(57) ABSTRACT

A pyridazine compound represented by formula [1]: which is useful as an active ingredient of a plant disease control agent can be produced, by steps of obtaining a compound represented by formula [3]: by reacting a compound represented by formula [4]: with a compound represented by formula [5]: obtaining a compound represented by formula [2]: by deprotecting the compound [3]; and reacting the compound [2] with a chlorinating agent.

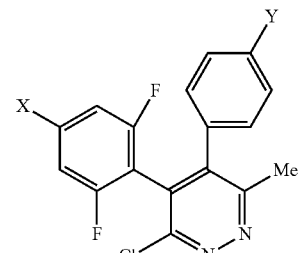

[1]

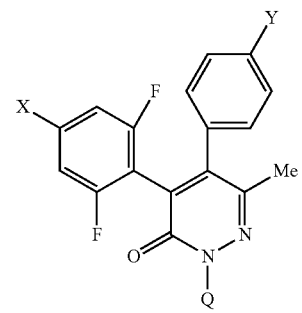

[3]

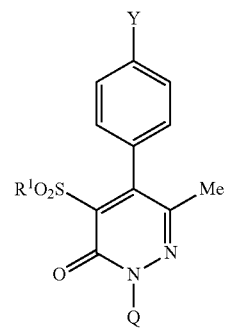

[4]

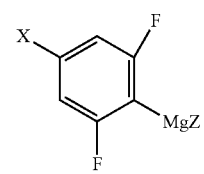

[5]

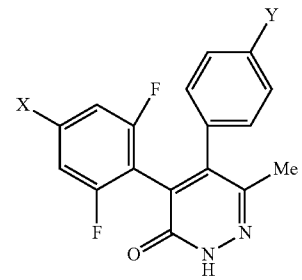

[2]

6 Claims, 4 Drawing Sheets
(4 of 4 Drawing Sheet(s) Filed in Color)

(56) References Cited

U.S. PATENT DOCUMENTS

| | | |
|---|---|---|
| 7,608,731 B2 | 10/2009 | Kertesz et al. |
| 2008/0194566 A1 | 8/2008 | Morishita et al. |
| 2009/0156608 A1 | 6/2009 | Souma et al. |
| 2013/0137683 A1 | 5/2013 | Matsuzaki |
| 2015/0376138 A1 | 12/2015 | Nakae et al. |

FOREIGN PATENT DOCUMENTS

| | | |
|---|---|---|
| EP | 2604116 A1 | 6/2013 |
| EP | 2 980 079 A1 | 2/2016 |
| WO | WO 2005/121104 A | 12/2005 |
| WO | WO 2007/080720 A1 | 7/2007 |
| WO | WO 2012/020774 A1 | 2/2012 |
| WO | WO 2014/129612 A1 | 8/2014 |
| WO | WO 2014/157021 A1 | 10/2014 |

OTHER PUBLICATIONS

International Search Report, issued in PCT/JP2014/062122, dated Aug. 21, 2014.
Bonnet et al., "Syntheses of Substituted Pyridines, Quinolines and Diazines via Palladium-catalyzed Cross-coupling of Aryl Grignard Reagents," Tetrahedron, vol. 58, Issue 22, May 27, 2002 (Available online Apr. 24, 2002), pp. 4429-4438.
Buchman et al., "Antihypertensive 5,6-Diarylpyridazin-3-ones," J. Med. Chem, vol. 23, No. 12, Dec. 31, 1980, pp. 1398-1405.
Chinese Office Action and Chinese Search Report, issued Sep. 1, 2016, for Chinese Application No. 201480029415.X, along with English translations.
Xu et al., "Synthesis and Herbicidal Activity of Novel 6-Methyl-4-(3-trifluoromethylphenyl)pyridazin-3(2H)-one," Chinese Journal of Organic Chemistry, vol. 30, No. 12, Dec. 31, 2010, pp. 1876-1883, with English abstract.

[Fig. 1]
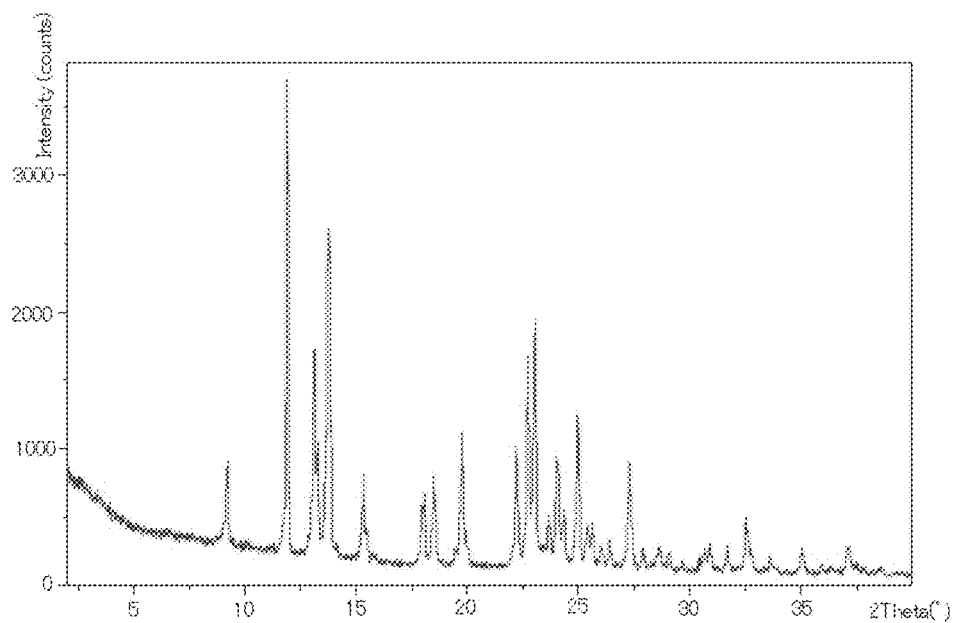
[Fig. 2]
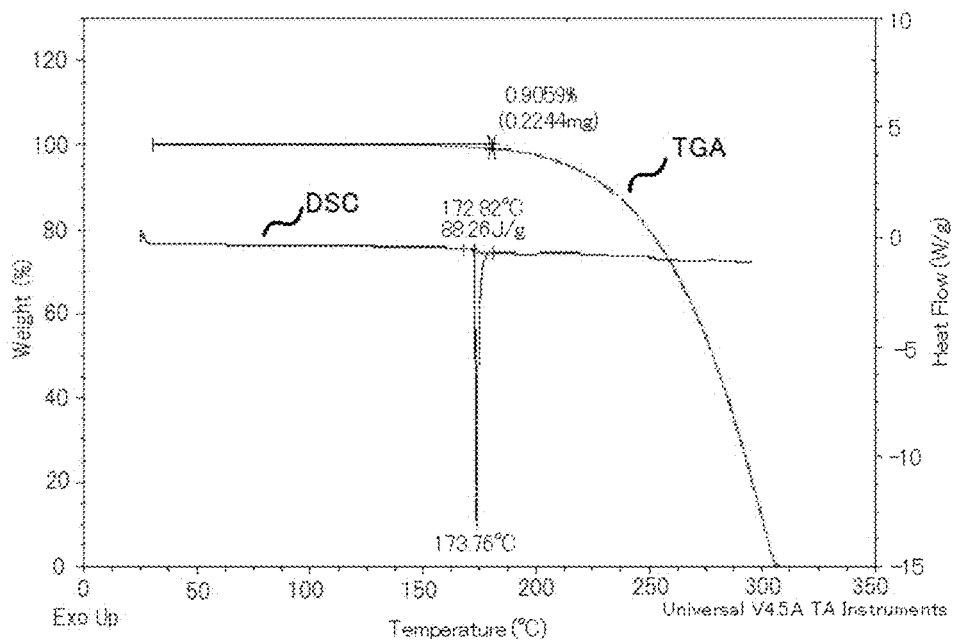

[Fig. 3]
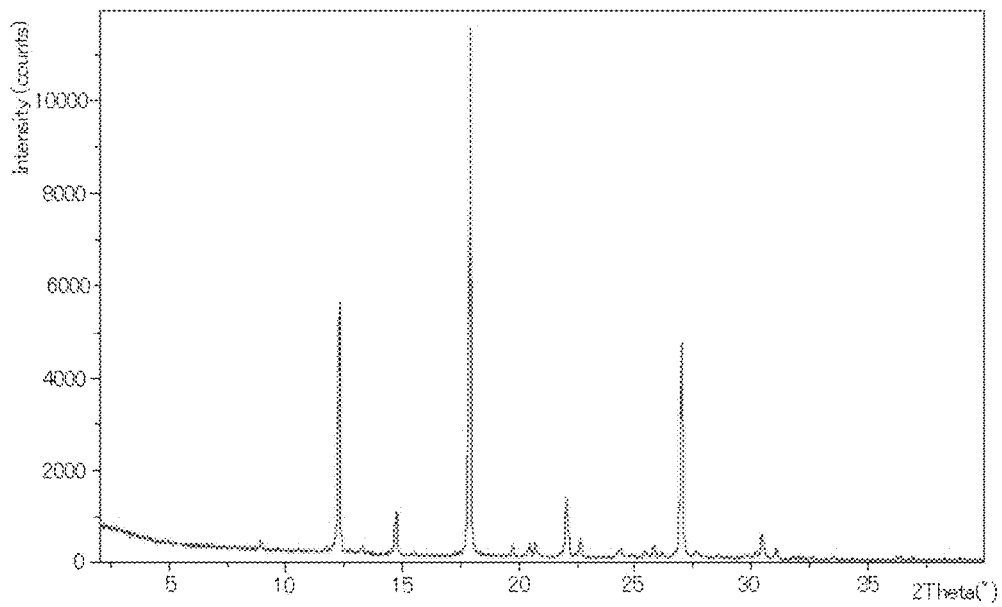
[Fig. 4]
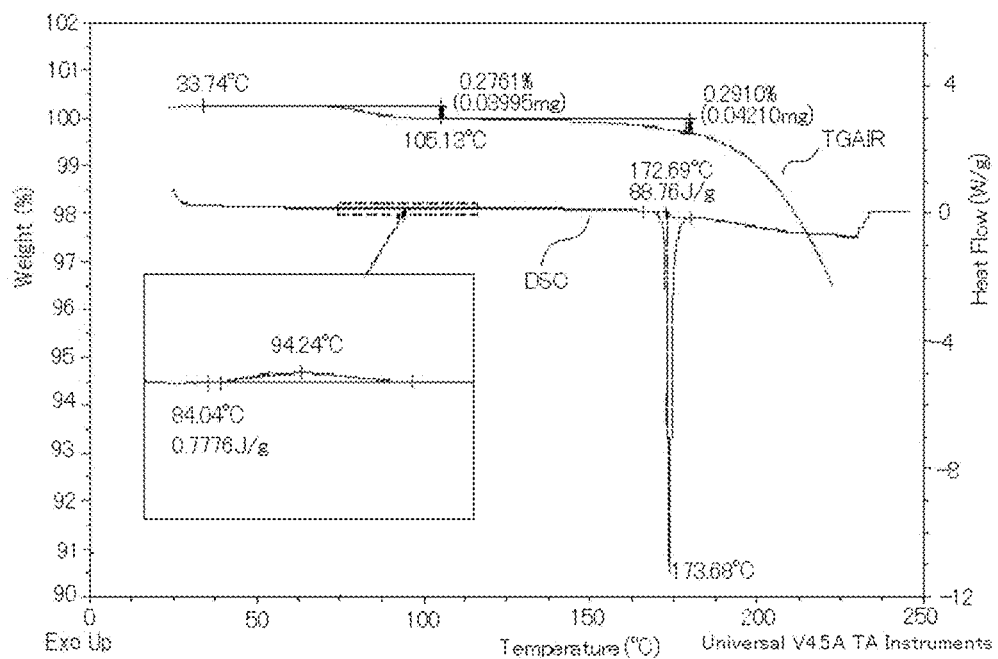

[Fig. 5]
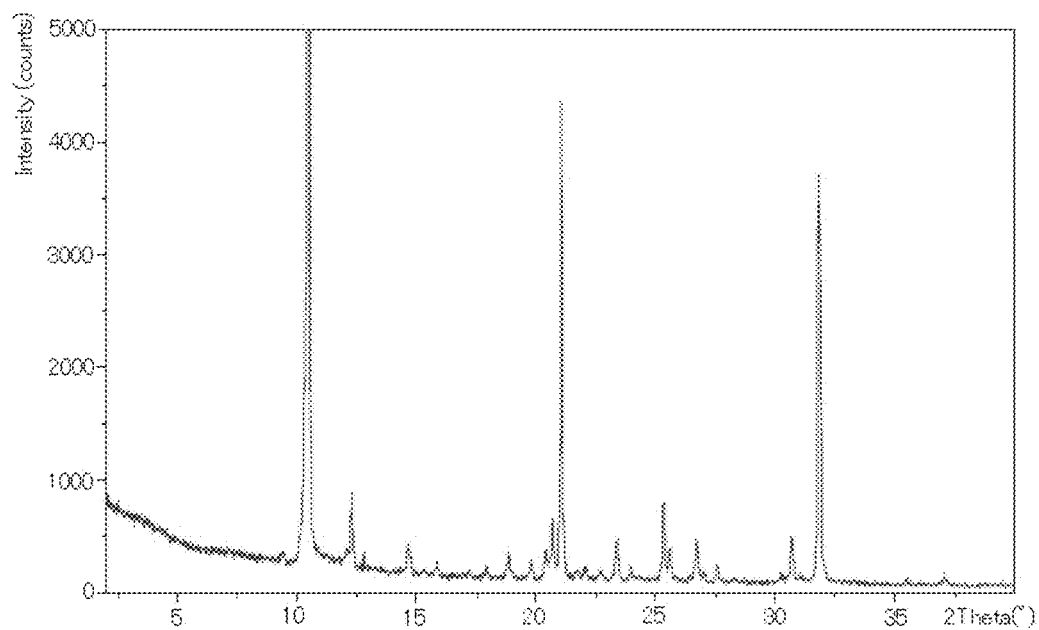
[Fig. 6]
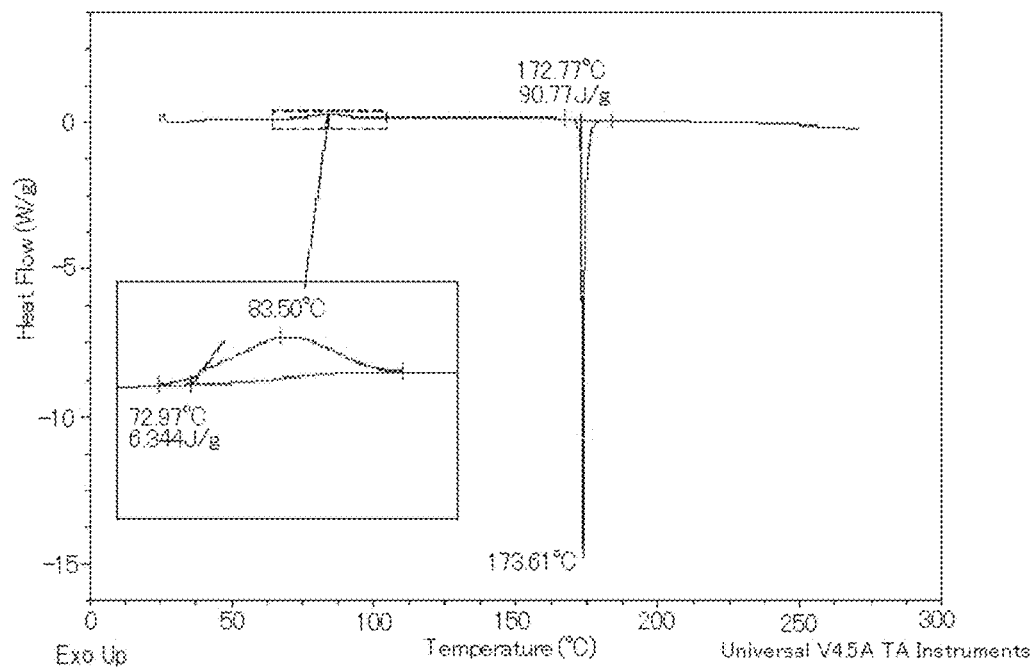

[Fig. 7]
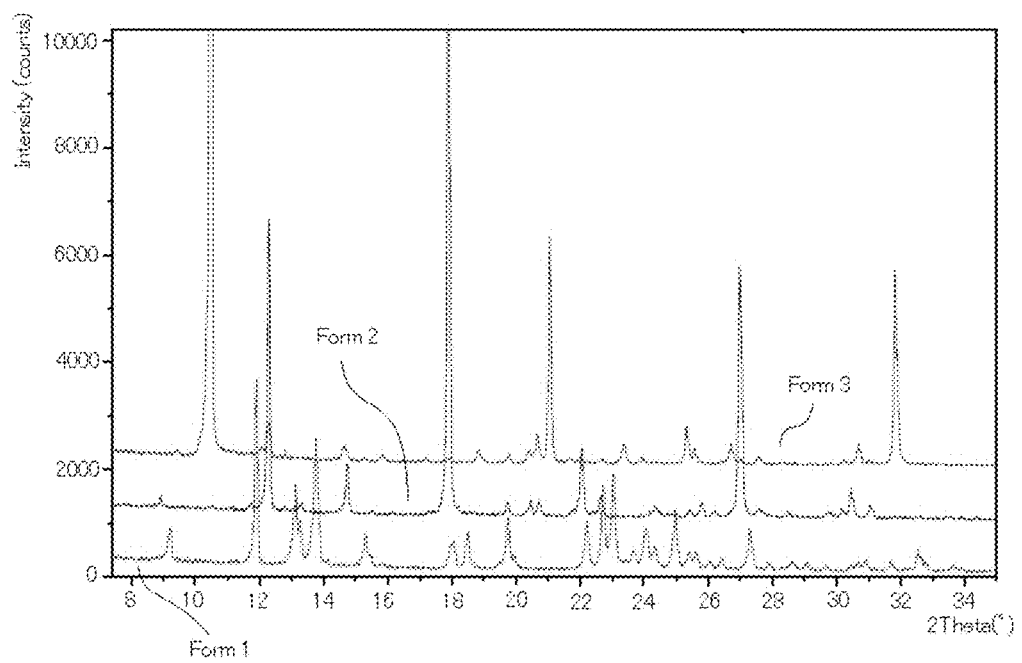

METHOD FOR PRODUCING PYRIDAZINE COMPOUND

TECHNICAL FIELD

The present invention relates to a method for producing a pyridazine compound, its production intermediate, and a method for producing the same.

BACKGROUND ART

In U.S. Pat. No. 7,569,518, a compound represented by formula [1]:

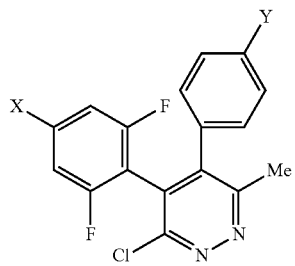

[1]

wherein X represents a hydrogen atom, a fluorine atom, a chlorine atom or a methyl group, and Y represents a hydrogen atom, a fluorine atom, a chlorine atom or a methyl group,
and the like are useful as an active ingredient of a plant disease control agent was described, and an advantageous production method thereof has been desired.

In addition, US 2009/156608 discloses a certain type of pyridazine compounds.

SUMMARY OF THE INVENTION

The present invention provides a method for producing a pyridazine compound represented by the formula [1], its production intermediate, and a method for producing the production intermediate.

More specifically, the present invention is as described below.

<<1>> A method for producing a compound [1] comprising steps of; obtaining a compound represented by formula [3]:

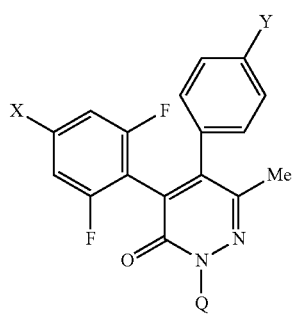

[3]

wherein Q represents a protective group that is an optionally halogenated C1 to C12 alkylsulfonyl group, a C6 to C24 arylsulfonyl group optionally substituted with at least one atom or group selected from group A, or a benzyl group in which at least one hydrogen atom on the benzene ring is optionally substituted with an atom or a group selected from group B, X represents a hydrogen atom, a halogen atom or a methyl group, and Y represents a hydrogen atom, a halogen atom or a methyl group, (hereinafter described as compound [3])

Group A: a group consisting of optionally halogenated C1 to C4 alkoxy groups, halogen atoms and a nitro group, Group B: a group consisting of optionally halogenated C1 to C4 alkyl groups, optionally halogenated C1 to C4 alkoxy groups, halogen atoms and a nitro group, by reacting a compound represented by formula [4]:

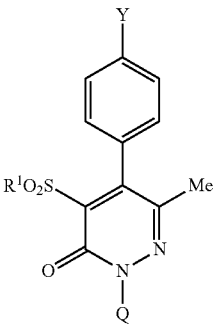

[4]

$R^1O_2S$— represents

wherein $R^1$ represents an optionally halogenated C1 to C12 alkyl group, or represents a C6 to C24 aryl group optionally substituted with at least one atom or group selected from group A, and Q and Y have the same meanings as described above, (hereinafter described as compound [4]) with a compound represented by formula [5]:

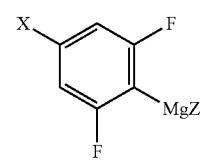

[5]

wherein X has the same meaning as described above, and Z represents a chlorine atom or bromine atom (hereinafter described as compound [5]);

obtaining a compound represented by formula [2]:

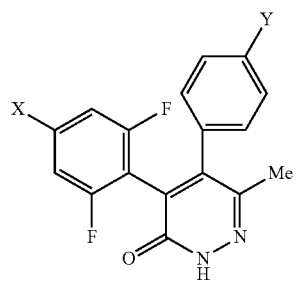

[2]

wherein X and Y have the same meanings as described above, (hereinafter described as compound [2]) by deprotecting the compound [3]; and obtaining a compound represented by formula [1]

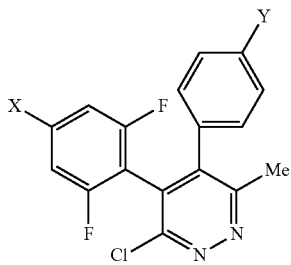

[1]

wherein X and Y have the same meanings as described above, (hereinafter described as compound [1]) by reacting the compound [2] with a chlorinating agent.

<<2>> A method for producing a compound [1] comprising steps of; obtaining a compound [3] by reacting a compound [4] with a compound [5]; and
mixing the compound [3] with phosphorus oxychloride and heating the mixture to obtain the compound [1].

<<3>> A method for producing a compound [1] comprising steps of; obtaining a compound represented by formula [3A]:

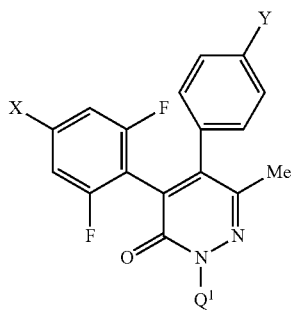

[3A]

wherein X and Y have the same meanings as described above, and
$Q^1$ represents an optionally halogenated C1 to C12 alkylsulfonyl group, or represents a C6 to C24 arylsulfonyl group optionally substituted with at least one atom or group selected from group A,
Group A: a group consisting of optionally halogenated C1 to C4 alkoxy groups, halogen atoms and a nitro group,
(hereinafter described as compound [3A]) by reacting a compound represented by formula [4A]:

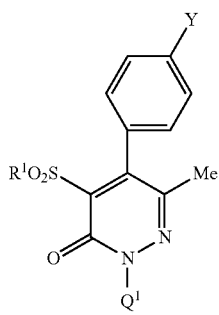

[4A]

$R^1O_2S$— represents

wherein $R^1$, Y and $Q^1$ have the same meanings as described above, (hereinafter described as compound [4A]) with a compound [5]; and obtaining the compound [1] by mixing the compound [3A] with a secondary amine and then adding a chlorinating agent to the mixture.

<<4>> Compound [3].

<<5>> A method for producing a compound [3] by reacting a compound [4] with a compound [5].

<<6>> Compound [4].

BRIEF DESCRIPTION OF DRAWINGS

The patent or application file contains at least one color drawing. Copies of this patent or patent application publication with color drawing will be provided by the USPTO upon request and payment of the necessary fee.

FIG. 1 is a PXRD Pattern of form 1 obtained in Reference Example 11.

FIG. 2 is a DSC/TGA Traces of form 1 obtained in Reference Example 11.

FIG. 3 is a PXRD Pattern of form 2 obtained in Reference Example 12.

FIG. 4 is a DSC/TGA Traces of form 2 obtained in Reference Example 12.

FIG. 5 is a PXRD Pattern of form 3 obtained in Reference Example 13.

FIG. 6 is a DSC/TGA Traces of form 3 obtained in Reference Example 13.

FIG. 7 is a PXRD Pattern Overlay for forms 1 to 3.

MODE FOR CARRYING OUT THE INVENTION

Hereinbelow, the present invention will be described in detail.

The halogen atom herein refers to a fluorine atom, a chlorine atom, a bromine atom, and an iodine atom. Among them, a chlorine atom and a fluorine atom are preferred.

The optionally halogenated C1 to C12 alkyl group herein represents a group in which at least one hydrogen atom of the C1 to C12 alkyl group is optionally substituted with a halogen atom, and when substituted with two or more halogen atoms, the halogen atoms may be different from each other. Examples of the optionally halogenated C1 to C12 alkyl group include a methyl group, an ethyl group, a propyl group, an isopropyl group, a butyl group, a tert-butyl group, a pentyl group, a neopentyl group, a 1-ethylpropyl group, a hexyl group, a heptyl group, an octyl group, a nonyl group, a decyl group, an undecyl group, a dodecyl group, an isoamyl group, a siamyl (1,2-dimethylpropyl) group, a thexyl (2,3-dimethyl-2-butyl) group, a cyclopropyl group, a cyclohexyl group, a 2,2,2-trichloroethyl group, a trifluoromethyl group, a pentafluoroethyl group, a 12-chlorododecyl group, a 3,3-dichloro-3-fluoropropyl group, and a dichlorofluoromethyl group. Among them, optionally halogenated C1 to C4 alkyl groups are preferred.

The C1 to C12 alkyl group herein represents a linear, branched or cyclic alkyl group having 1 to 12 carbon atoms, and examples thereof include a methyl group, an ethyl group, a propyl group, an isopropyl group, a butyl group, a tert-butyl group, a pentyl group, a neopentyl group, a 1-ethylpropyl group, a hexyl group, a heptyl group, an octyl group, a nonyl group, a decyl group, an undecyl group, a dodecyl group, an isoamyl group, a siamyl group, a thexyl group, a cyclopropyl group, a cyclohexyl group, a cyclohexylmethyl group, a norbornyl group and an adamantyl group. Among them, C1 to C4 alkyl groups are preferred.

The optionally halogenated C1 to C4 alkyl group herein represents a group in which at least one hydrogen atom of the C1 to C4 alkyl group is optionally substituted with a halogen atom, and when substituted with two or more halogen atoms, the halogen atoms may be different from each other. Examples of the optionally halogenated C1 to C4 alkyl group include a methyl group, an ethyl group, a propyl group, an isopropyl group, a cyclopropyl group, a butyl group, a tert-butyl group, a 2,2,2-trichloroethyl group, a trifluoromethyl group, a pentafluoroethyl group, a 3,3-dichloro-3-fluoropropyl group, and a dichlorofluoromethyl.

The C1 to C4 alkyl group herein represents a linear, branched or cyclic alkyl group having 1 to 4 carbon atoms, and examples thereof include a methyl group, an ethyl group, a propyl group, an isopropyl group, a cyclopropyl group, a butyl group, and a tert-butyl group.

The C6 to C24 aryl group optionally substituted with at least one atom or group selected from group A herein represents a group in which at least one hydrogen atom of a C6 to C24 aryl group is optionally substituted with an atom or a group selected from group A, and when substituted with two or more atoms or groups, the atoms or groups may be different from each other. Examples of the optionally substituted C6 to C24 aryl group include a phenyl group, a tolyl group, a nitrophenyl group, a chlorophenyl group, an anisyl group, a chlorofluorophenyl group, a dimethoxyphenyl group, a pentafluorophenyl group, a trifluorophenyl group, a trifluoromethylphenyl group, a trifluoromethoxyphenyl group, and a chloroterphenyl group. Among them, optionally substituted C6 to C14 aryl groups are preferred, and particularly an optionally substituted phenyl group is preferred.

The aryl group herein represents a substituent obtained by removing one hydrogen atom from an aromatic ring of an aromatic hydrocarbon, and the carbon number represents the number including the alkyl group directly bonded to the aromatic ring.

The C6 to C24 aryl group herein represents a monocyclic or polycyclic aryl group having 6 to 24 carbon atoms, and these rings may be condensed. Examples of the C6 to C24 aryl groups include a phenyl group, a tolyl group, a mesityl group, a naphthyl group, a biphenyl group, an anthracenyl group, a pyrenyl group, a terphenyl group, a binaphthyl group, a quaterphenyl group, a 3',5'-diphenylbiphenyl group, an indanyl group, and a di-tert-butylphenyl group. Among them, C6 to C14 aryl groups are preferred.

The C6 to C14 aryl group in which at least one hydrogen atom is optionally substituted with an atom or a group selected from group A herein represents a group in which at least one hydrogen atom of a C6 to C14 aryl group is optionally substituted with an atom or a group selected from group A, and when substituted with two or more atoms or groups, the atoms or groups may be different from each other. Examples of the optionally substituted C6 to C14 aryl group include a phenyl group, a tolyl group, a chlorophenyl group, an anisyl group, and a chlorofluorophenyl group.

The C6 to C14 aryl group herein represents a monocyclic or polycyclic aryl group having 6 to 14 carbon atoms, and these rings may be condensed. Examples of the C6 to C14 aryl group include a phenyl group, a tolyl group, a naphthyl group, a biphenyl group, an indanyl group, and a di-tert-butylphenyl group. Among them, a phenyl group and a 4-tolyl group are preferred.

The optionally halogenated C1 to C12 alkylsulfonyl group herein represents a group in which at least one hydrogen atom of the C1 to C12 alkylsulfonyl group is optionally substituted with a halogen atom, and when substituted with two or more halogen atoms, the halogen atoms may be different from each other. Examples of the optionally halogenated C1 to C12 alkylsulfonyl group include a methylsulfonyl group, a cyclohexylsulfonyl group, a trifluoromethylsulfonyl group, a 2,2,2-trichloroethylsulfonyl group, a pentafluoroethylsulfonyl group, a 3,3-dichloro-3-fluoropropylsulfonyl group, and a 12-chlorododecylsulfonyl group. Among them, optionally halogenated C1 to C4 alkylsulfonyl groups are preferred.

The C1 to C12 alkylsulfonyl group herein represents a linear, branched or cyclic alkylsulfonyl group having 1 to 12 carbon atoms, and examples thereof include a methylsulfonyl group, an ethylsulfonyl group, a propylsulfonyl group, a tert-butylsulfonyl group, a pentylsulfonyl group, a hexylsulfonyl group, a heptylsulfonyl group, an octylsulfonyl group, a nonylsulfonyl group, a decylsulfonyl group, an undecylsulfonyl group, a dodecylsulfonyl group, an isoamylsulfonyl group, a siamylsulfonyl group, a thexylsulfonyl group, a cyclopropylsulfonyl group, a cyclohexylsulfonyl group, a cyclohexylmethylsulfonyl group, a norbornylsulfonyl group, and an adamantylsulfonyl group. Among them, C1 to C4 alkylsulfonyl groups are preferred.

The optionally halogenated C1 to C4 alkylsulfonyl group herein represents a group in which at least one hydrogen atom of the C1 to C4 alkylsulfonyl group is optionally substituted with a halogen atom, and when substituted with two or more halogen atoms, the halogen atoms may be different from each other. Examples of the optionally halogenated C1 to C4 alkylsulfonyl group include a methylsulfonyl group, an ethylsuifonyl group, a cyclopropylsulfonyl group, a trifluoromethylsulfonyl group, a 2,2,2-trichloroethylsulfonyl group, and a pentafluoroethylsulfonyl group. Among them, a methylsulfonyl group, an ethylsulfonyl group and a trifluoromethylsulfonyl group are preferred.

The C1 to C4 alkylsulfonyl group herein represents a linear, branched or cyclic alkylsulfonyl group having 1 to 4 carbon atoms, and examples thereof include a methylsulfonyl group, an ethylsulfonyl group, a propylsulfonyl group, a cyclopropylsulfonyl group, and a tert-butylsulfonyl group.

The C6 to C24 arylsulfonyl group optionally substituted with at least one atom or group selected from group A herein represents a C6 to C24 arylsulfonyl group in which at least one hydrogen atom of the C6 to C24 arylsulfonyl group is optionally substituted with an atom or a group selected from group A, and when substituted with two or more atoms or groups, the atoms or groups may be different from each other. Examples of the optionally substituted C6 to C24 arylsulfonyl group include a phenylsulfonyl group, a tolylsulfonyl group, a naphthylsulfonyl group, a mesitylsulfonyl group, a biphenylsulfonyl group, an anthracenylsulfonyl group, a pyrenylsulfonyl group, a terphenylsulfonyl group, a binaphthylsulfonyl group, a quaterphenylsulfonyl group, a 3',5'-diphenylbiphenylsulfonyl group, a nitrophenylsulfonyl group, a chlorophenylsulfonyl group, an anisylsulfonyl group, a chlorofluorophenylsulfonyl group, a dimethoxyphenylsulfonyl group, a pentafluorophenylsulfonyl group, a trifluoromethylphenylsulfonyl group, a trifluoromethoxyphenylsulfonyl group, and a chloroterphenylsulfonyl group. Among them, the optionally substituted C6 to C14 arylsulfonyl groups are preferred, and particularly an optionally substituted phenylsulfonyl group is preferred.

The C6 to C24 arylsulfonyl group herein represents a monocyclic or polycyclic arylsulfonyl group having 6 to 24 carbon atoms, and these rings may be condensed. Examples of the C6 to C24 arylsulfonyl groups include a phenylsulfonyl group, a tolylsulfonyl group, a naphthylsulfonyl group, a biphenylsulfonyl group, an anthracenylsulfonyl group, a pyrenylsulfonyl group, a terphenylsulfonyl group, a binaphthylsulfonyl group, a quaterphenylsulfonyl group, a 3',5'-diphenylbiphenylsulfonyl group, an indanylsulfonyl group, and a di-tert-butylphenylsulfonyl group. Among them, C6 to C14 arylsulfonyl groups are preferred.

The C6 to C14 arylsulfonyl group optionally substituted with at least one atom or group selected from group A herein represents a C6 to C14 arylsulfonyl group in which at least one hydrogen atom of the C6 to C14 arylsulfonyl group is optionally substituted with an atom or a group selected from group A, and when substituted with two or more atoms or groups, the atoms or groups may be different from each other. Examples of the optionally substituted C6 to C14 arylsulfonyl group include a phenylsulfonyl group, a tolylsulfonyl group, a naphthylsulfonyl group, a nitrophenylsulfonyl group, a chlorophenylsulfonyl group, an anisylsulfonyl group, a chlorofluorophenylsulfonyl group, a dimethoxyphenylsulfonyl group, a pentafluorophenylsulfonyl group, a trifluoromethylphenylsulfonyl group, and a trifluoromethoxyphenylsulfonyl group. Among them, a phenylsulfonyl group and a 4-tolylsulfonyl group are preferred.

The C6 to C14 arylsulfonyl group herein represents a monocyclic or polycyclic arylsulfonyl group having 6 to 14 carbon atoms, and these rings may be condensed. Examples of the C6 to C14 arylsulfonyl group include a phenylsulfonyl group, a tolylsulfonyl group, a naphthylsulfonyl group, a biphenylsulfonyl group, an indanylsulfonyl group, and a di-tert-butylphenylsulfonyl group. Among them, a phenylsulfonyl group and a 4-tolylsulfonyl group are preferred.

The benzyl group in which at least one hydrogen atom on the benzene ring is optionally substituted with an atom or a group selected from group B herein represents a benzyl group in which at least one hydrogen atom on the benzene ring is optionally substituted with an atom or a group selected from group B, and when substituted with two or more atoms or groups, the atoms or groups may be different from each other. Examples of the optionally substituted benzyl group include a benzyl group, a tolylmethyl group (methylbenzyl group), a chlorophenylmethyl group (chlorobenzyl group), an anisylmethyl group (methoxybenzyl group), a dimethoxyphenylmethyl group (dimethoxybenzyl group), a nitrophenylmethyl group (nitrobenzyl group), a trifluloromethylphenylmethyl group (trifluloromethylbenzyl group), a cyclopropyloxyphenylmethyl group, a (2,2-dichlorocyclopropyloxy)phenylmethyl group, and a trifluoromethoxyphenylmethyl group (trifluoromethoxybenzyl group). Among them, a benzyl group, a tolylmethyl group, a chlorophenylmethyl group and an anisylmethyl group are preferred, and a benzyl group and a 4-anisylmethyl group are particularly preferred.

The optionally halogenated C1 to C4 alkoxy group herein represents a group in which at least one hydrogen atom of a linear, branched or cyclic alkoxy group having 1 to 4 carbon atoms is optionally substituted with a halogen atom, and when substituted with two or more halogen atoms, the halogen atoms may be different from each other. Examples of the linear, branched or cyclic alkoxy group having 1 to 4 carbon atoms include a methoxy group, an ethoxy group, a propyloxy group, an isopropyloxy group, a cyclopropyloxy group, a butoxy group, and a tert-butoxy group, and examples of the optionally halogenated C1 to C4 alkoxy group include a methoxy group, a 2,2,2-trichloroethoxy group, a trifluoromethoxy group, an ethoxy group, a propyloxy group, an isopropyloxy group, a 2,2-dichlorocyclopropyloxy group, a butoxy group, a tert-butoxy group, a pentafluoroethoxy group, and a 3,3-dichloro-3-fluoropropyloxy group.

Examples of the chlorinating agent include phosphorus oxychloride, phosphorus trichloride, phosphorus pentachloride, sulfuryl chloride, thionyl chloride, phosgene and the mixtures thereof, and among them, phosphorus oxychloride is preferred.

The secondary amine herein represents a secondary chain amine and a secondary cyclic amine, and the secondary chain amine includes dimethylamine, diethylamine, diisopropylamine and the like, and the secondary cyclic amine include pyrrolidine, piperidine, morpholine, and azoles unsubstituted on the nitrogen atom (e.g., imidazole, 1,2,4-triazole). Among them, secondary cyclic amines are preferred, and piperidine and morpholine are particularly preferred.

Examples of the embodiment of the compound [1] include the following compounds:
Compound, wherein X and Y are each a hydrogen atom in the formula [1].

Examples of the embodiment of the compound [2] include the following compounds:
Compound, wherein X and Y are each a hydrogen atom in the formula [2].

Examples of the embodiment of the compound [3] include the following compounds:
Compounds, wherein X and Y are each a hydrogen atom in the formula [3];
Compounds, wherein Q is a C6 to C24 arylsulfonyl group in which at least one hydrogen atom is optionally substituted with an atom or a group selected from group A, or a benzyl group in which at least one hydrogen atom on the benzene ring is optionally substituted with an atom or a group selected from group B, in the formula [3];
Compounds, wherein Q is a C6 to C24 arylsulfonyl group or a benzyl group in the formula [3];
Compounds, wherein Q is a C6 to C14 arylsulfonyl group or a benzyl group in the formula [3];
Compounds, wherein Q is a 4-tolylsulfonyl group, a phenylsulfonyl group or a benzyl group in the formula [3];
Compounds, wherein Q is a 4-tolylsulfonyl group or a phenylsulfonyl group in the formula [3];
Compounds, wherein Q is a 4-tolylsulfonyl group in the formula [3];
Compounds, wherein Q is a phenylsulfonyl group in the formula [3];
Compounds, wherein Q is a benzyl group in the formula [3].

Compounds, wherein X and Y are each a hydrogen atom, and Q is a C6 to C24 arylsulfonyl group in which at least one hydrogen atom is optionally substituted with an atom or a group selected from group A, or a benzyl group in which at least one hydrogen atom on the benzene ring is optionally substituted with an atom or a group selected from group B, in the formula [3];
Compounds, wherein X and Y are each a hydrogen atom, and Q is a C6 to C24 arylsulfonyl group or a benzyl group, in the formula [3];
Compounds, wherein X and Y are each a hydrogen atom, and Q is a C6 to C14 arylsulfonyl group or a benzyl group, in the formula [3];
Compounds, wherein X and Y are each a hydrogen atom, and Q is a 4-tolylsulfonyl group, a phenylsulfonyl group or a benzyl group, in the formula [3];
Compounds, wherein X and Y are each a hydrogen atom, and Q is a 4-tolylsulfonyl group or a phenylsulfonyl group, in the formula [3];
Compound, wherein X and Y are each a hydrogen atom, and Q is a phenylsulfonyl group, in the formula [3];

Compound, wherein X and Y are each a hydrogen atom, and Q is a 4-tolylsulfonyl group, in the formula [3];

Compound, wherein X and Y are each a hydrogen atom, and Q is a benzyl group, in the formula [3].

Compound, wherein X is a fluorine atom, Y is a hydrogen atom, and Q is a phenylsulfonyl group, in the formula [3];

Compound, wherein X is a fluorine atom, Y is a hydrogen atom, and Q is a 4-tolylsulfonyl group, in the formula [3];

Compound, wherein X is a fluorine atom, Y is a hydrogen atom, and Q is a benzyl group, in the formula [3];

Compound, wherein X is a fluorine atom, Y is a chlorine atom, and Q is a 4-tolylsulfonyl group, in the formula [3];

Compound, wherein X is a hydrogen atom, Y is a chlorine atom, and Q is a benzyl group, in the formula [3];

Examples of the embodiment of the compound [4] include the following compounds:

Compounds, wherein Y is a hydrogen atom in the formula [4];

Compounds, wherein $R^1$ is a C1 to C12 alkyl group in which at least one hydrogen atom is optionally substituted with a halogen atom, or a C6 to C24 aryl group in which at least one hydrogen atom is optionally substituted with an atom or a group selected from group A, in the formula [4];

Compounds, wherein $R^1$ is a C1 to C12 alkyl group or a C6 to C24 aryl group in the formula [4];

Compounds, wherein $R^1$ is a C1 to C6 alkyl group in which at least one hydrogen atom is optionally substituted with a halogen atom, or a C6 to C14 aryl group in which at least one hydrogen atom is optionally substituted with an atom or a group selected from group A, in the formula [4];

Compounds, wherein $R^1$ is a C1 to C6 alkyl group or a C6 to C14 aryl group in the formula [4];

Compounds, wherein $R^1$ is a methyl group, a phenyl group or a 4-tolyl group in the formula [4];

Compounds, wherein $R^1$ is a methyl group in the formula [4];

Compounds, wherein Q is a 4-tolylsulfonyl group in the formula [4];

Compounds, wherein $R^1$ is a methyl group, and Q is a phenylsulfonyl group, in the formula [4];

Compounds, wherein $R^1$ is a methyl group, and Q is a 4-tolylsulfonyl group, in the formula [4];

Compounds, wherein Y is a hydrogen atom, Q is a C6 to C24 arylsulfonyl group in which at least one hydrogen atom is optionally substituted with an atom or a group selected from group A, or a benzyl group in which at least one hydrogen atom on the benzene ring is optionally substituted with an atom or a group selected from group B, and $R^1$ is an optionally halogenated C1 to C6 alkyl group, or a C6 to C24 aryl group in which at least one hydrogen atom is optionally substituted with an atom or a group selected from group A, in the formula [4];

Compounds, wherein Y is a hydrogen atom, Q is a C6 to C24 arylsulfonyl group or a benzyl group, and $R^1$ is a C1 to C6 alkyl group or a C6 to C24 aryl group, in the formula [4];

Compounds, wherein Y is a hydrogen atom, Q is a C6 to C14 arylsulfonyl group or a benzyl group, and $R^1$ is a C1 to C6 alkyl group or a C6 to C14 aryl group, in the formula [4];

Compounds, wherein Y is a hydrogen atom, Q is a 4-tolylsulfonyl group or a benzyl group, and $R^1$ is a methyl group, a phenyl group or a 4-tolyl group, in the formula [4];

Compounds, wherein Y is a hydrogen atom, Q is a C6 to C24 arylsulfonyl group in which at least one hydrogen atom is optionally substituted with an atom or a group selected from group A, and $R^1$ is an optionally halogenated C1 to C6 alkyl group, in the formula [4];

Compounds, wherein Y is a hydrogen atom, Q is a C6 to C24 arylsulfonyl group, and $R^1$ is a C1 to C6 alkyl group, in the formula [4];

Compounds, wherein Y is a hydrogen atom, Q is a C6 to C14 arylsulfonyl group, and $R^1$ is a C1 to C6 alkyl group, in the formula [4];

Compound, wherein Y is a hydrogen atom, Q is a 4-tolylsulfonyl group, and $R^1$ is a methyl group, in the formula [4];

Compounds, wherein Y is a hydrogen atom, Q is a benzyl group in which at least one hydrogen atom on the benzene ring is optionally substituted with an atom or a group selected from group B, and $R^1$ is an C6 to C24 aryl group in which at least one hydrogen atom is optionally substituted with an atom or a group selected from group A, in the formula [4];

Compounds, wherein Y is a hydrogen atom, Q is a benzyl group, and $R^1$ is a C6 to C24 aryl group, in the formula [4];

Compounds, wherein Y is a hydrogen atom, Q is a benzyl group, and $R^1$ is a C6 to C14 aryl group, in the formula [4];

Compounds, wherein Y is a hydrogen atom, Q is a benzyl group, and $R^1$ is a phenyl group or a 4-tolyl group, in the formula [4];

Compounds, wherein $R^1$ is a phenyl group in the formula [4];

Compounds, wherein $R^1$ is a phenyl group, and Q is a 4-tolylsulfonyl group, in the formula [4];

Compounds, wherein $R^1$ is a phenyl group or a 4-tolyl group, and Q is a benzyl group, in the formula [4];

Compounds, wherein $R^1$ is a phenyl group, and Q is a benzyl group, in the formula [4];

Compounds, wherein Y is a hydrogen atom, and Q is a benzyl group, in the formula [4];

Compound, wherein Y is a hydrogen atom, Q is a 4-tolylsulfonyl group, and $R^1$ is a phenyl group, in the formula [4];

Compound, wherein $R^1$ is a methyl group, Y is a chlorine atom, and Q is a 4-tolylsulfonyl group, in the formula [4];

Compound, wherein $R^1$ is a methyl group, Y is a hydrogen atom, and Q is a benzyl group, in the formula [4];

Compound, wherein $R^1$ is a methyl group, Y is a hydrogen atom, and Q is a phenylsulfonyl group, in the formula [4];

Compound, wherein $R^1$ is a methyl group, Y is a hydrogen atom, and Q is a 4-tolylsulfonyl group, in the formula [4];

Compound, wherein $R^1$ is a phenyl group, Y is a chlorine atom, and Q is a 4-tolylsulfonyl group, in the formula [4];

Compound, wherein $R^1$ is a phenyl group, Y is a hydrogen atom, and Q is a benzyl group, in the formula [4];

Compound, wherein $R^1$ is a phenyl group, Y is a hydrogen atom, and Q is a phenylsulfonyl group, in the formula [4];

Compound, wherein $R^1$ is a phenyl group, Y is a hydrogen atom, and Q is a 4-tolylsulfonyl group, in the formula [4];

Examples of the embodiment of the compound [5] include the following compounds:

Compounds, wherein X is a hydrogen atom in the formula [5].

Next, each step of the method of the present invention will be described. In the formula, symbols have the same meanings as described above.

(Production Method 1)

The step of producing a compound [3] will be described.

The compound [3] can be produced by reacting a compound [4] with a compound [5].

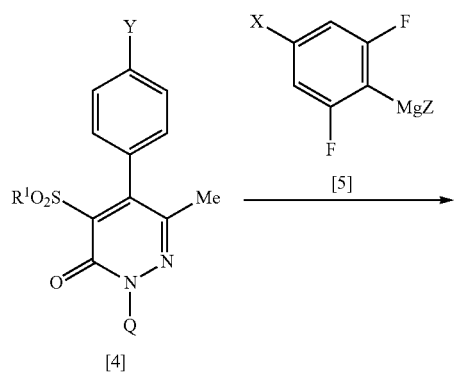

[4]

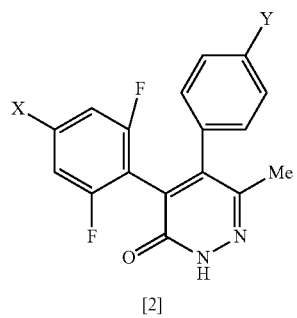

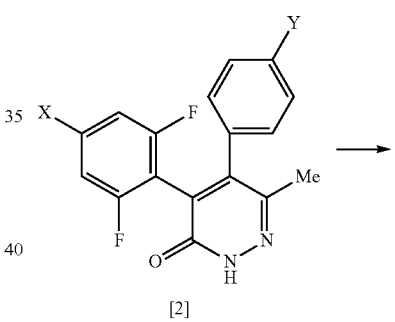

[3]

wherein the symbols have the same meanings as described above.

The reaction is usually carried out in a solvent. Examples of the solvent include hydrocarbons such as toluene and xylene, ethers such as tetrahydrofuran, cyclopentyl methyl ether and ethylene glycol dimethyl ether, and mixtures thereof.

The reaction temperature is usually in the range of −20 to 30° C., and more preferably in the range of 0 to 50° C. The reaction time is usually in the range of 1 to 100 hours.

The amount of the compound [5] used in the reaction is a proportion of usually 1 to 10 mol and preferably 1 to 1.2 mol, based on 1 mol of the compound [4].

After completion of the reaction, for example, the reaction mixture is mixed with hydrochloric acid or sulfuric acid, and then the precipitate is collected by filtration, or extracted with an organic solvent, and the resulting organic layer is subjected to operations such as drying and concentration, whereby the compound [3] can be isolated.

The isolated compound [3] can also be further purified by column chromatography, recrystallization or the like.

(Production Method 2)

The step of producing a compound [2] from a compound [3] will be described.

The compound [2] can be produced by deprotecting the compound [3].

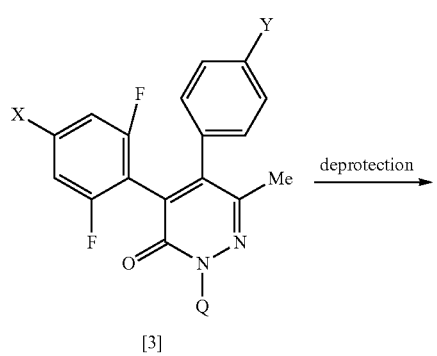

[3]

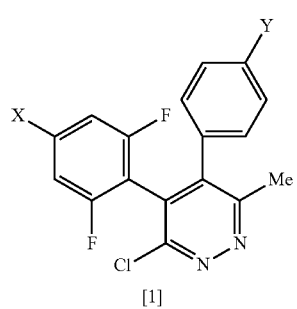

[2]

wherein the symbols have the same meanings as described above.

The compound [2] can be produced by deprotecting the compound [3], according to a known method, for example, the method described in Greene et al., Protective Groups in Organic Chemistry 4$^{th}$. WILEY INTERSCIENCE, and Journal of Heterocyclic chemistry. 2003, 203, and the like.

(Production Method 3)

The step of producing a compound [1] from a compound [2] will be described.

The compound [1] can be produced by reacting the compound [2] with a chlorinating agent.

[2]

[1]

wherein the symbols have the same meanings as described above.

The reaction can be carried out according to the method described in U.S. Pat. No. 7,569,518.

(Production Method 4)

The step of producing a compound [1] from a compound [3] will be described.

The compound [1] can be produced by mixing the compound [3] with phosphorus oxychloride and heating the mixture.

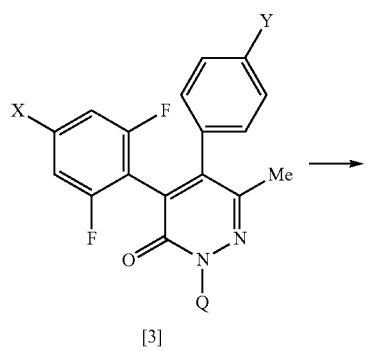

[3]

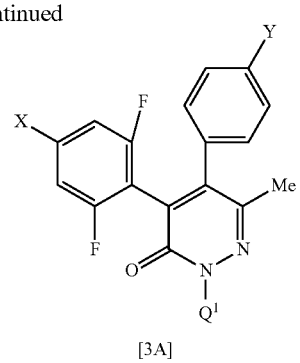

[3A]

wherein the symbols have the same meanings as described above.

The compound [3A] can be produced, according to Production Method 1, replacing the compound [4] by the compound [4A].

(Production Method 6)

The step of producing a compound [1] from a compound [3A] will be described.

The compound [1] can be produced by mixing the compound [3A] with a secondary amine to allow a deprotection of $Q^1$ and then adding a chlorinating agent to the resultant.

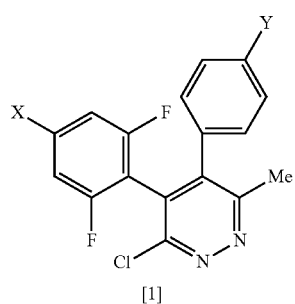

[1]

wherein the symbols have the same meanings as described above.

The reaction is usually carried out in a solvent. Examples of the solvent include hydrocarbons such as toluene and xylene, and halogenated hydrocarbons such as chloroform and chlorobenzene, and phosphorus oxychloride can also be used as a solvent.

The reaction temperature is usually in the range of 60 to 180° C., and the reaction time is usually in the range of 1 to 100 hours.

The use amount of the phosphorus oxychloride is a proportion of 1 to 20 mol and preferably 1 to 5 mol, based on 1 mol of the compound [3].

After completion of the reaction, for example, the reaction mixture is mixed with water or a basic aqueous solution such as an aqueous solution of sodium hydroxide, and then the precipitate is collected by filtration, or extracted with an organic solvent, and the resulting organic layer is subjected to operations such as drying and concentration, whereby compound [1] can be isolated. The isolated compound [1] can also be further purified by column chromatography, recrystallization or the like.

(Production Method 5)

The step of producing a compound [3A] from a compound [4A] will be described.

The compound [3A] can be produced by reacting the compound [4A] with a compound [5].

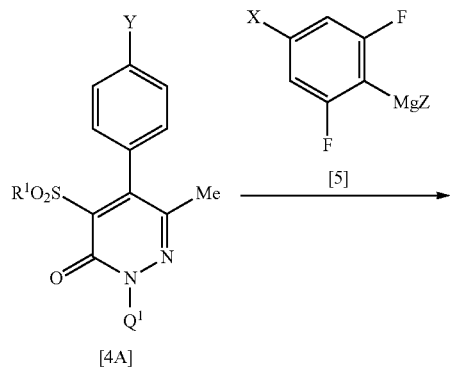

[4A]

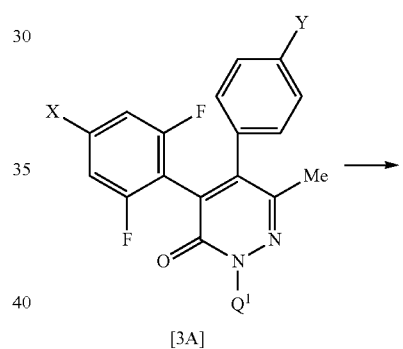

[3A]

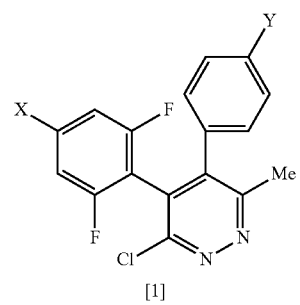

[1]

wherein the symbols have the same meanings as described above.

The reaction is usually carried out in a solvent. Examples of the solvent include hydrocarbons such as toluene and xylene, halogenated hydrocarbons such as chlorobenzene, ethers such as tetrahydrofuran, cyclopentyl methyl ether and ethylene glycol dimethyl ether, and mixtures thereof.

The reaction temperature is usually in the range of 20 to 150° C., and the reaction time is usually in the range of 1 to 100 hours.

Examples of the secondary amine include chain amines such as dimethylamine, diethylamine and diisopropylamine, and cyclic amines such as pyrrolidine, piperidine, morpholine, imidazole and 1,2,4-triazole, and among them, cyclic amines are preferred, and piperidine and morpholine are particularly preferred.

The use amount of the secondary amine is a proportion of 1 to 2 mol and preferably 1 to 1.2 mol, based on 1 mol of the compound [3A].

Examples of the chlorinating agent include phosphorus oxychloride, phosphorus trichloride, phosphorus pentachloride, phosgene and the mixtures thereof, and phosphorus oxychloride is preferred.

The use amount of the chlorinating agent is a proportion of 1 to 10 mol, preferably 1 to 3 mol, and more preferably 1 to 1.1 mol, based on 1 mol of the compound [3A].

After completion of the reaction, for example, the reaction mixture is mixed with water or a basic aqueous solution such as an aqueous solution of sodium hydroxide, and then the precipitate is collected by filtration, or extracted with an organic solvent, and the resulting organic layer is subjected to operations such as drying and concentration, whereby compound [1] can be isolated. The isolated compound [1] can also be further purified by column chromatography, recrystallization or the like.

(Reference Production Method 1)

Next, the step of producing a compound [4] will be described.

The compound [4] can be produced by protecting a nitrogen atom of a compound represented by formula [6]:

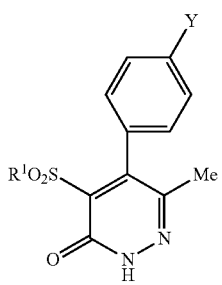

[6]

$R^1O_2S$— represents

wherein Y and $R^1$ have the same meanings as described above, (hereinafter described as compound [6])

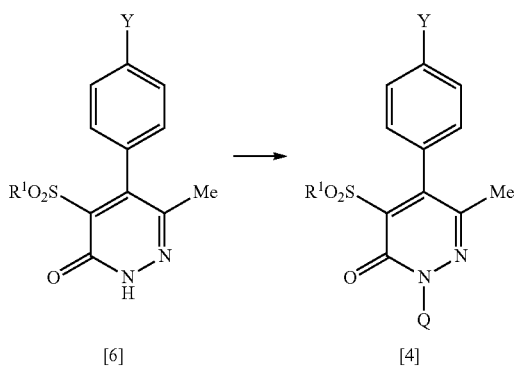

wherein the symbols have the same meanings as described above.

When a compound, wherein Q is $Q^1$ in the compound [4] (i.e., compound [4A]), is produced, a compound [4A] can be produced by reacting a compound represented by formula [7]:

$$Q^1\text{-Cl} \qquad [7]$$

wherein the symbols have the same meanings as described above, (hereinafter described as compound [7]) with the compound [6].

Examples of the compound [7] include methylsulfonyl chloride, ethylsulfonyl chloride, propylsulfonyl chloride, tert-butylsulfonyl chloride, pentylsulfonyl chloride, hexylsulfonyl chloride, heptylsulfonyl chloride, octylsulfonyl chloride, nonylsulfonyl chloride, decylsulfonyl chloride, undecylsulfonyl chloride, dodecylsulfonyl chloride, isoamylsulfonyl chloride, thexylsulfonyl chloride, cyclopropylsulfonyl chloride, cyclohexylsulfonyl chloride, cyclohexylmethylsulfonyl chloride, norbornylsulfonyl chloride, adamantylsulfonyl chloride, tosyl chloride, phenylsulfonyl chloride, naphthylsulfonyl chloride, mesitylsulfonyl chloride, biphenylsulfonyl chloride, anthracenylsulfonyl chloride, pyrenylsulfonyl chloride, terphenyl sulfonyl chloride, binaphthylsulfonyl chloride, quaterphenyl sulfonyl chloride, 3',5'-diphenylbiphenylsulfonyl chloride, nitrophenylsulfonyl chloride, chlorophenylsulfonyl chloride, anisylsulfonyl chloride, chlorofluorophenylsulfonyl chloride, dimethoxyphenylsulfonyl chloride, and pentafluorophenylsulfonyl chloride.

The reaction is usually carried out in a solvent. Examples of the solvent include ethers such as tetrahydrofuran, cyclopentyl methyl ether and ethylene glycol dimethyl ether, hydrocarbons such as toluene and xylene, halogenated hydrocarbons such as chlorobenzene, aprotic polar solvents such as dimethylformamide, N-methylpyrrolidin-2-one, ethyl acetate, butyl acetate, acetonitrile, acetone and 2-butanone, and mixtures thereof.

The reaction is usually carried out in the presence of a base, for example, inorganic base. Examples of the base include hydrides of an alkali metal such as sodium hydride, hydroxides of an alkali metal such as sodium hydroxide and potassium hydroxide, carbonates of an alkali metal such as potassium carbonate and sodium carbonate, organic salts such as triethylamine, pyridine, dimethylaniline and N,N-dimethylaminopyridine (DMAP), and mixtures thereof.

The reaction temperature is usually in the range of −20 to 100° C., and the reaction time is usually in the range of 1 to 100 hours.

The use amount of the compound [7] is a proportion of 1 to 2 mol and preferably 1 to 1.2 mol in the aspect of cost, based on 1 mol of the compound [6].

The use amount of the base is a proportion of 1 to 100 mol and preferably 1 to 1.2 mol, based on 1 mol of the compound [6].

After completion of the reaction, for example, the reaction mixture is mixed with water or mixed with hydrochloric acid or sulfuric acid and neutralized, and then extracted with an organic solvent, and the resulting organic layer is subjected to operations such as drying and concentration, whereby compound [4] can be isolated. The isolated compound [4] can also be further purified by column chromatography, recrystallization or the like.

A compound, wherein Q is a benzyl group in which at least one hydrogen atom on the benzene ring is optionally substituted with an atom or a group selected from group B, in the compound [4], can be produced by reacting a benzyl chloride such as benzyl chloride, methylbenzyl chloride, methoxybenzyl chloride, dimethoxybenzyl chloride or nitrobenzyl chloride, or a benzyl bromide such as benzyl bromide, methylbenzyl bromide, methoxybenzyl bromide, dimethoxybenzyl bromide or nitrobenzyl bromide, with the compound [6].

The reaction is usually carried out in a solvent. Examples of the solvent include hydrocarbons such as toluene and xylene, halogenated hydrocarbons such as chlorobenzene and chloroform, ethers such as tetrahydrofuran, cyclopentyl methyl ether and ethylene glycol dimethyl ether, aprotic polar solvents such as dimethylformamide, N-methylpyrrolidin-2-one, ethyl acetate, butyl acetate, acetonitrile, acetone and 2-butanone, alcohols such as methanol, and mixtures thereof.

The reaction is usually carried out in the presence of a base. Examples of the base include hydrides of an alkali metal such as sodium hydride, hydroxides of an alkali metal such as sodium hydroxide and potassium hydroxide, inorganic salts such as carbonates of an alkali metal such as potassium carbonate and sodium carbonate, and organic salts such as triethylamine, pyridine and dimethylaniline.

The reaction temperature is usually in the range of −20° C. to the boiling point of the solvent, and the reaction time is usually in the range of 1 to 100 hours.

The use amount of the benzyl chloride or benzyl bromide is a proportion of 1 to 10 mol and preferably 1 to 1.2 mol, based on 1 mol of the compound [6].

The use amount of the base is a proportion of 1 to 100 mol and preferably 1 to 1.2 mol, based on 1 mol of the compound [6].

After completion of the reaction, for example, the reaction mixture is mixed with water or mixed with hydrochloric acid or sulfuric acid and neutralized, and then extracted with an organic solvent, and the resulting organic layer is subjected to operations such as drying and concentration, whereby compound [6] can be isolated. The isolated compound [6] can also be further purified by column chromatography, recrystallization or the like.

The compound [6] can be produced, according to a known method, for example, the method described in US 2009/156608.

(Reference Production Method 2)

Next, the step of producing a compound [5] will be described.

The compound [5] can be produced by a known method, for example, by reacting a compound represented by formula [8] (hereinafter described as compound [8]) with magnesium (Mg) or isopropyl magnesium chloride (i-PrMgCl).

wherein i-Pr represents an isopropyl group, and Z has the same meaning as described above.

The compound [5] can be used for the next step, without being isolated and purified.

The reaction is usually carried out in a solvent. Examples of the solvent include ethers such as tetrahydrofuran, cyclopentyl methyl ether and ethylene glycol dimethyl ether, hydrocarbons such as toluene and xylene, and mixtures thereof.

The reaction temperature is usually in the range of −20 to 30° C., and preferably 0 to 5° C., and the reaction time is usually in the range of 1 to 100 hours.

The use amount of Mg is a proportion of 1 to 1.5 mol and preferably 1 to 1.05 mol, based on 1 mol of the compound [8].

When Mg is used in the reaction, 1,2-dibromoethane or the like is preferably added as a reaction initiator, and the use amount thereof is preferably a proportion of 0.001 to 0.01 mol, based on 1 mol of the compound [8].

When Mg is used in the reaction, the solvent is preferably ethers such as tetrahydrofuran.

The use amount of the isopropyl magnesium chloride used is usually in the range of 1 to 1.5 mol and more preferably in the range of 1 to 1.05 mol, based on 1 mol of the compound [8].

EXAMPLES

Hereinbelow, the present invention will be described further in detail by examples, but the present invention is not limited to these examples.

The symbols herein represent the following meanings.

Ms represents a methane sulfonyl group.
Ts represents a 4-tolylsulfonyl group.
Ph represents a phenyl group.
Bn represents a benzyl group.
MTBE represents a tert-butyl methyl ether.
THF represents tetrahydrofuran.

Example 1

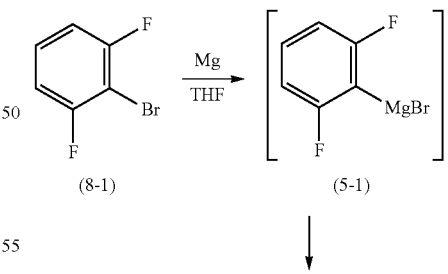

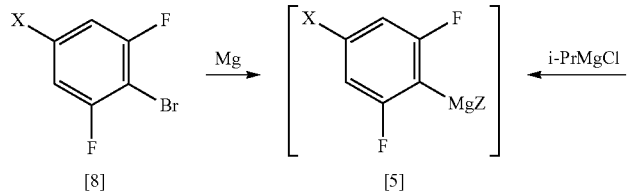 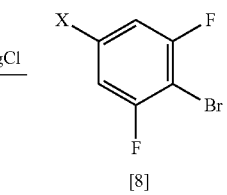

-continued

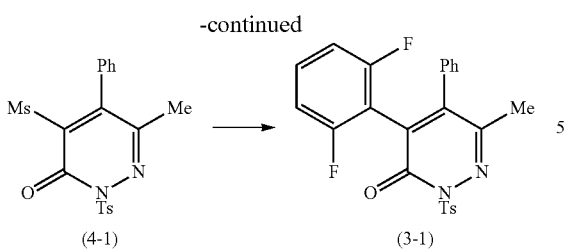

Under a nitrogen atmosphere, 0.3 g of Mg and 15 mL of THF were mixed and stirred at 0° C. To the mixture were added the whole amount of solution of 0.08 g of 1,2-dibromoethane in 0.5 mL of THF and 1.5 mL of solution of 2.0 g of 1-bromo-2,6-difluorobenzene in 10.0 mL of THF (hereinafter described as compound (8-1)). After 5 minutes, 2.5 mL of the solution of the compound (8-1) was further added. After stirring the mixture for a while, the residue amount of the solution of the compound (8-1) was added dropwise, and the mixture was stirred at 0° C. for 2 hours. A solution of 2,6-difluorophenylmagnesium bromide prepared as above (hereinafter described as compound (5-1)) was transferred to a dropping funnel kept at 0° C.

In another reaction vessel, 4.0 g of 4-methanesulfonyl-6-methyl-5-phenyl-2-(4-tolylsulfonyl)-2H-pyridazin-3-one (hereinafter described as compound (4-1)) and 10.0 mL of THF were mixed and stirred at 0° C. Thereto was added dropwise a solution of the compound (5-1) over about 15 minutes, and the mixture was further stirred at 0° C. for 6 hours. The reaction mixture was returned to room temperature, and then 10% hydrochloric acid and hexane were added. The mixture was vigorously stirred and then filtered. The substance on the filter paper was sequentially washed with water, MTBE and hexane, and the substance on the filter paper was dried under reduced pressure at 50° C., to obtain 4.0 g (yield 92%) of 4-(2,6-difluorophenyl)-6-methyl-5-phenyl-2-(4-tolylsulfonyl)-2H-pyridazin-3-one (hereinafter described as compound (3-1)) as a white solid.
Compound (3-1)
$^1$H-NMR (CDCl$_3$, TMS) δ (ppm): 8.12 (2H, d, J=8.3 Hz), 7.36 (2H, d, J=8.1 Hz), 7.29-7.24 (3H, m), 7.19-7.11 (1H, m), 7.07-7.03 (2H, m), 6.70 (2H, dd, J=8.3, 7.3 Hz), 2.45 (3H, s), 2.23 (3H, s).

Example 2

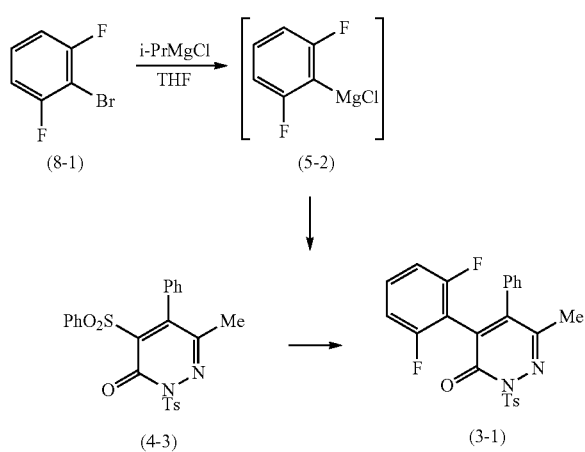

Experiment 1: a solution of 105 mg of the compound (8-1) in 1.0 mL of THF was stirred at 0° C. under a nitrogen atmosphere, 0.3 mL of solution of 2 M isopropylmagnesium chloride-THF was added, and the mixture was stirred at the same temperature for 1 hour to prepare a solution of 2,6-difluorophenylmagnesium chloride (hereinafter described as compound (5-2)), and then the solution was kept at 0° C.

Experiment 2: a solution of 105 mg of the compound (8-1) in 1.0 mL of THF was stirred at 0° C. under a nitrogen atmosphere, 0.3 mL of solution of 2 M isopropylmagnesium chloride-THF was added, and the mixture was stirred at the same temperature for 1 hour to prepare a solution of the compound (5-2), and then the solution was kept at 0° C.

In another reaction vessel, a mixture of 200 mg of 6-methyl-5-phenyl-4-phenylsulfonyl-2-(4-tolylsulfonyl)-2H-pyridazin-3-one (hereinafter described as compound (4-3)) and 1.0 mL of THF was stirred at 0° C. under a nitrogen atmosphere, and the whole amount of the solution of the compound (5-2) prepared in Experiment 1 was added. The mixture was stirred at the same temperature for 1.5 hours, then the whole amount of the solution of the compound (5-2) prepared in Experiment 2 was added, and the mixture was stirred for further 1 hour. Hydrochloric acid, MTBE and ethyl acetate were added to the mixture, and the separated organic layer was washed with saturated saline. The organic layer was dried over anhydrous sodium sulfate, and the yield of the compound (3-1) obtained by LC-IS (Internal Standard) quantification was about 100%.

Example 3

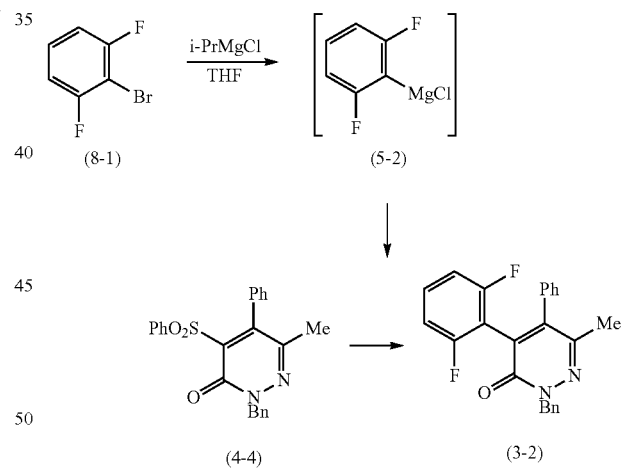

Experiment 1: a solution of 108 mg of the compound (8-1) in 1.0 mL of THF was stirred at 0° C. under a nitrogen atmosphere, 0.3 mL of solution of 2 M isopropylmagnesium chloride-THF was added, and the mixture was stirred at the same temperature for 1 hour to prepare a solution of the compound (5-2), and then the solution was kept at 0° C.

Experiment 2: a solution of 108 mg of the compound (8-1) in 1.0 mL of THF was stirred at 0° C. under a nitrogen atmosphere, 0.3 mL of solution of 2 M isopropylmagnesium chloride-THF was added, and the mixture was stirred at the same temperature for 1 hour to prepare a solution of the compound (5-2), and then the solution was kept at 0° C.

In another reaction vessel, a mixture of 200 mg of 2-benzyl-6-methyl-5-phenyl-4-phenylsulfonyl-2H-pyridazin-3-one (hereinafter described as compound (4-4)) and 1.0 mL of THF was stirred at 0° C. under a nitrogen atmosphere, and the whole amount of a solution of the compound (5-2) prepared in Experiment 1 was added. The mixture was stirred at the same temperature for 1.5 hours, and then the whole amount of the solution of the compound (5-2) prepared in Experiment 2 was added, and the mixture was stirred for further 1 hour. Hydrochloric acid and ethyl acetate were added to the mixture, the separated aqueous layer was extracted with ethyl acetate, and then the organic layer was mixed, and washed with saturated saline. The organic layer was dried over anhydrous sodium sulfate, and the yield of 2-benzyl-4-(2,6-difluorophenyl)-6-methyl-5-phenyl-2H-pyridazin-3-one (hereinafter described as compound (3-2)) obtained by LC-IS quantification was 96%.

Compound (3-2)

$^1$H-NMR (CDCl$_3$, TMS) δ (ppm): 7.55 (2H, d, J=6.6 Hz), 7.39-7.31 (3H, m), 7.26-7.25 (3H, m), 7.16-7.14 (1H, m), 7.08-7.07 (2H, m), 6.73 (2H, dd, J=8.3, 7.3 Hz), 5.39 (2H, s), 2.12 (3H, s).

Example 4

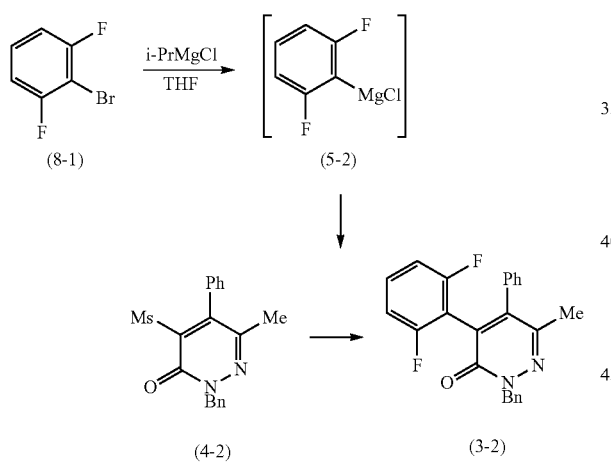

A solution of 0.3 g of the compound (8-1) in 4.0 mL of THF was stirred at 0° C. under a nitrogen atmosphere, and 0.8 mL of solution of 2.0 M isopropylmagnesium chloride-THF was added, and then the mixture was stirred at the same temperature for 1 hour. Thereafter, 0.5 g of 2-benzyl-4-methanesulfonyl-6-methyl-5-phenyl-2H-pyridazin-3-one (hereinafter described as compound (4-2)) was added, and the mixture was stirred for further 16 hours. To the mixture was added 1 N hydrochloric acid, then the mixture was returned to room temperature, and 20 mL of 1 N hydrochloric acid and 30 mL of water were added, and then the mixture was extracted twice with 60 mL of ethyl acetate. The extracts were mixed, and concentrate under reduced pressure, and then the residue was purified by silica gel column chromatography (elution solvent: hexane-ethyl acetate) to obtain 309 mg of the compound (3-2) (yield 60%).

Example 5

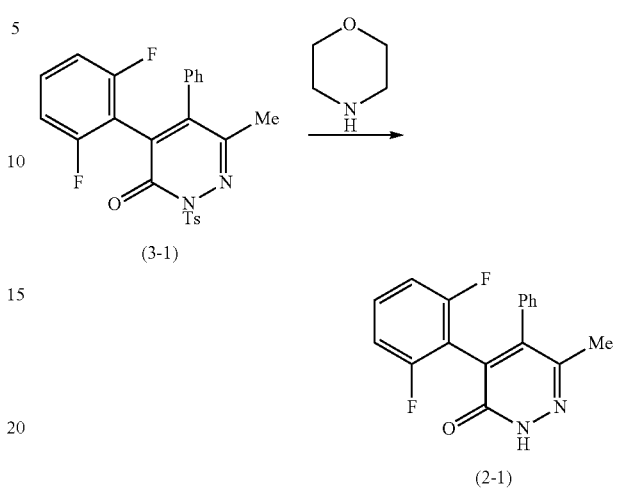

A mixture of 235 mg of the compound (3-1), 56 mg of morpholine and 856 mg of toluene was heated and stirred at 50° C. for 2.5 hours, at 80° C. for 4 hours, and at 100° C. for 2.5 hours. The reaction mixture was cooled to room temperature, and then 1.0 mL of hexane was added, and the mixture was filtered. The residue was washed with hexane, and then dried under reduced pressure, to obtain 227 mg of a white solid. Based on $^1$H-NMR, the yield of the compound (2-1) was 74%.

Example 6

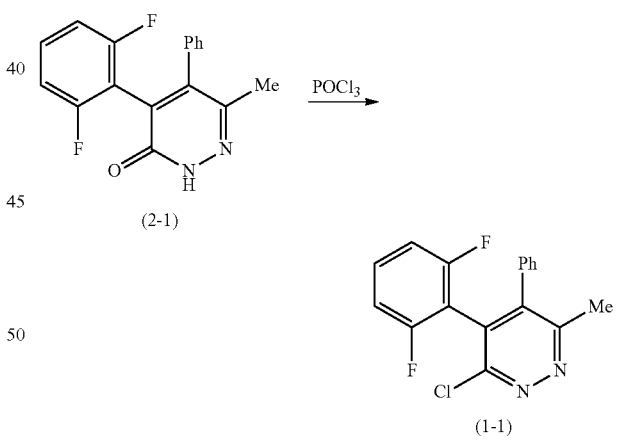

A mixture of 136 mg of 4-(2,6-difluorophenyl)-6-methyl-5-phenyl-2H-pyridazin-3-one (hereinafter described as compound (2-1)) and 865 mg of toluene was heated and stirred at 100° C. under a nitrogen atmosphere, and 0.1 mL of phosphorus oxychloride was added. The mixture was heated and stirred for further 4.5 hours, and then cooled to room temperature, 10% aqueous solution of sodium hydroxide and ethyl acetate were added to the mixture. The separated aqueous layer was extracted twice with ethyl acetate. The combined organic layer was subjected to LC-IS quantification, and the yield of the compound (1-1) was found to be 85%.

Example 7

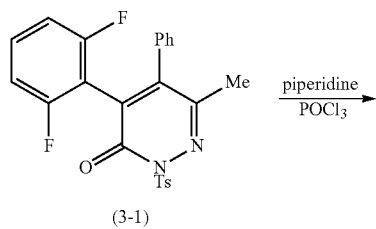

A mixture of 2.0 g of the compound (3-1), 399 mg of piperidine and 10.0 g of toluene was heated and stirred at 100° C. for 5 hours under a nitrogen atmosphere, and then cooled to room temperature. Thereto, 0.4 mL of phosphorus oxychloride was added, and the mixture was heated and stirred at 100° C. for 9 hours. To the mixture was added 0.1 mL of phosphorus oxychloride at 100° C., and the mixture was further heated and stirred at 100° C. for 4 hours, then cooled to room temperature, 9.4 g of a 10% aqueous solution of sodium hydroxide was added to separate the mixture. The aqueous layer was extracted with toluene, and the aqueous layer was further extracted with ethyl acetate. The organic layers were combined, and the yield of 3-chloro-4-(2,6-difluorophenyl)-6-methyl-5-phenylpyridazine (hereinafter described as compound (1-1)) obtained by LC-IS quantification was 80%. The organic layer was dried over anhydrous sodium sulfate, and then concentrated under reduced pressure to obtain 2.5 g of crude product. The crude product was recrystallized from methanol-MTBE to obtain 0.7 g of subject matter. Yield: 51%. Furthermore, the filtrate was concentrated under reduced pressure to obtain 1.6 g of residue. (yield 29% by LC-IS quantification)

Example 8

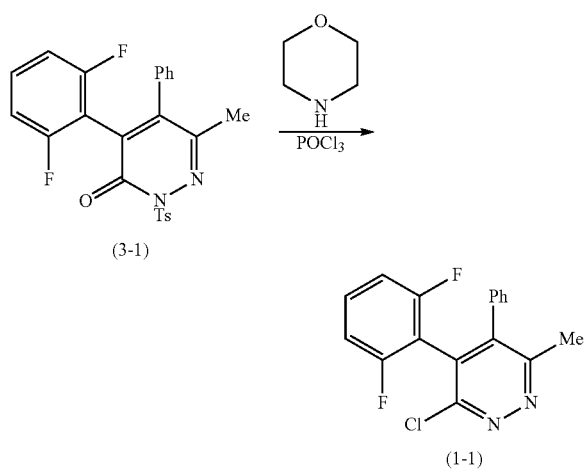

A mixture of 202 mg of the compound (3-1), 41 mg of morpholine and 1.0 g of toluene was heated and stirred at 100° C. for 8 hours under a nitrogen atmosphere, and then 0.2 mL of 3% morpholine/toluene solution was added, and the mixture was further heated and stirred at 100° C. for 4.5 hours. The mixture was cooled to room temperature, and 0.05 mL of phosphorus oxychloride was added. Further, the mixture was heated and stirred at 100° C. for 7 hours, and then cooled to room temperature. To the reaction mixture was added acetonitrile, and then the reaction mixture was subjected to LC-IS quantification. The yield of the compound (1-1) was found to be 80%.

Reference Example 1

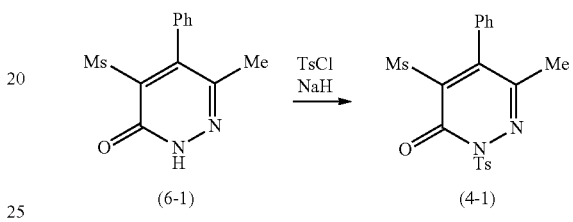

Under a nitrogen atmosphere, 16 g of 55% sodium hydride and 870 g of THF were mixed under a nitrogen atmosphere and stirred. The mixture was cooled to 0° C., 87 g of 4-methanesulfonyl-6-methyl-5-phenyl-2H-pyridazin-3-one (hereinafter described as compound (6-1)) was added, followed by 73 g of tosyl chloride, and then the mixture was stirred at the same temperature for 2 hours. To the reaction mixture was added 88 g of 1 N hydrochloric acid, and then the mixture was concentrated under reduced pressure. To the residue were added 2 kg of water and 7 kg of ethyl acetate to separate the mixture, and the organic layer was washed with 1 kg of saturated saline. The organic layer was concentrated under reduced pressure, 412 g of ethanol was added thereto, the mixture was stirred and then filtered, and then the substance on the filter paper was washed with 412 g of ethanol. The resulting residue was dried under reduced pressure to obtain 131 g of the compound (4-1) (yield 95%).
Compound (4-1)
$^1$H-NMR (CDCl$_3$, TMS) δ (ppm): 8.11 (2H, d, J=7.9 Hz), 7.47-7.45 (3H, m), 7.40 (2H, d, J=8.0 Hz), 7.16-7.14 (2H, m), 3.28 (3H, s), 2.48 (3H, s), 2.09 (3H, s).

Reference Example 2

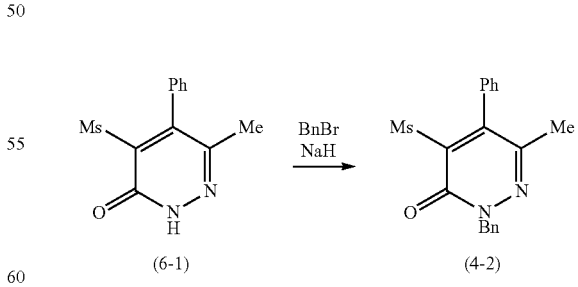

Under a nitrogen atmosphere, 18 g of 55% sodium hydride and 950 g of DMF (N,N-dimethylformamide) were mixed and stirred. The mixture was cooled to 0° C., 97 g of the compound (6-1) was added little by little, subsequently 72 g of benzyl bromide was added dropwise, and then the mixture was stirred for 2 hours. To the reaction mixture was added 73 g of 1 N hydrochloric acid, and 1.7 kg of ethyl acetate and 1.0 kg of water were further added to separate the mixture. The aqueous layer was extracted twice with 1 L of ethyl acetate, and the organic layers were mixed, washed with 1 L of saturated saline, dried over anhydrous magnesium sulfate, and concentrated under reduced pressure. To the concentrated residue were added 524 g of ethanol and 53 g of chloroform, and the mixture was heated to 80° C., and then cooled to room temperature. The precipitated solid was filtered, and the substance on the filter paper was washed twice with 128 g of ethanol, and then the substance on the filter paper was dried under reduced pressure to obtain 112 g of the compound (4-2) (yield 86%).
Compound (4-2)
$^1$H-NMR (CDCl$_3$, TMS) δ (ppm): 7.53 (2H, d, J=7.1 Hz), 7.46-7.44 (3H, m), 7.40-7.34 (3H, m), 7.17-7.14 (2H, m), 5.37 (2H, s), 3.33 (3H, s), 2.02 (3H, s).

Reference Example 3

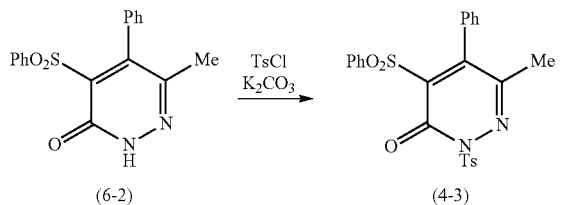

A mixture of 2.0 g of 6-methyl-5-phenyl-4-phenylsulfonyl-2H-pyridazin-3-one (hereinafter described as compound (6-2)), 1.4 g of tosyl chloride, 1.1 g of potassium carbonate and 10 g of acetonitrile was heated and stirred at 80° C. for 4 hours under a nitrogen atmosphere, then cooled to room temperature, and water and MTBE were added to the mixture. The separated organic layer was washed with saturated saline, dried over anhydrous sodium sulfate, and then concentrated under reduced pressure to obtain 2.6 g of the compound (4-3). Yield: 89% Compound (4-3)
$^1$H-NMR (CDCl$_3$, TMS) δ (ppm): 8.03 (2H, d, J=7.8 Hz), 7.89 (2H, d, J=8.1 Hz), 7.59 (1H, t, J=7.1 Hz), 7.53-7.49 (3H, m), 7.46 (2H, t, J=7.6 Hz), 7.34 (2H, d, J=8.1 Hz), 7.20-7.16 (2H, m), 2.46 (3H, s), 2.04 (3H, s).

Reference Example 4

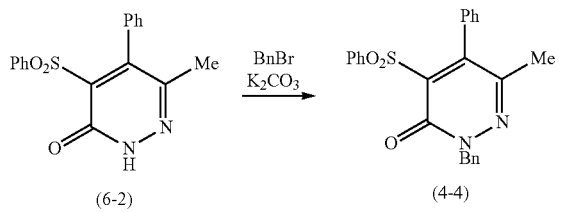

A mixture of 2.0 g of the compound (6-2), 1.0 g of potassium carbonate, 10 g of methanol and 1.4 g of benzyl bromide was stirred at room temperature for 4.5 hours, and then MTBE, water and ethyl acetate were added to the mixture to separate an organic layer. The separated aqueous layer was extracted with ethyl acetate. The organic layers were combined, washed with saturated saline, dried over anhydrous sodium sulfate, and then concentrated under reduced pressure to obtain 2.9 g of crude product. The crude product was subjected to silica gel column chromatography (elution solvent: hexane-MTBE) to obtain 1.5 g of the compound (4-4) (yield 43%).
Compound (4-4)
$^1$H-NMR (CDCl$_3$, TMS) δ (ppm): 8.00-7.97 (2H, m), 7.60 (1H, t, J=7.3 Hz), 7.52-7.47 (5H, m), 7.41-7.37 (2H, m), 7.32-7.27 (3H, m), 7.22 (2H, dd, J=7.8, 1.5 Hz), 5.25 (2H, s), 1.97 (3H, s).

Reference Example 5

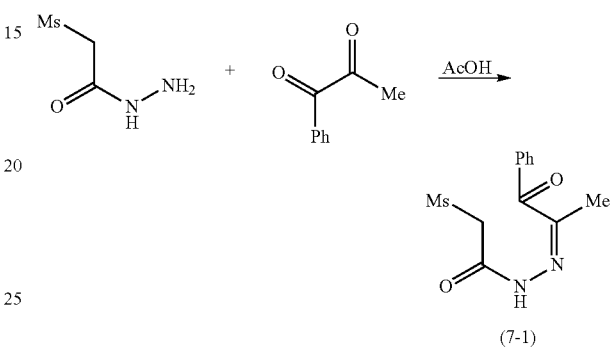

To a mixture of 190 ml of ethanol, 30.0 g of 2-methanesulfonylacetylhydrazide and 32.1 g of 1-phenylpropane-1,2-dione, 23.7 g of acetic acid was added at room temperature under a nitrogen atmosphere. The mixture was stirred at room temperature for 6 hours, and then the precipitated solid was collected by filtration. The filtered residue was washed with ethanol, thereby obtaining 50.5 g (yield 90%) of 2-methanesulfonylacetic acid 1-methyl-2-oxo-2-phenylethylidenehydrazide (hereinafter described as compound (7-1)).
Compound (7-1)
$^1$H-NMR (CDCl$_3$, TMS) δ (ppm): 2.23 (3H, s), 3.11 (3H, s), 4.35 (2H, s), 7.46-7.50 (2H, m), 7.56-7.58 (1H, m), 7.94-7.61 (2H, m), 9.23 (1H, m).

Reference Example 6

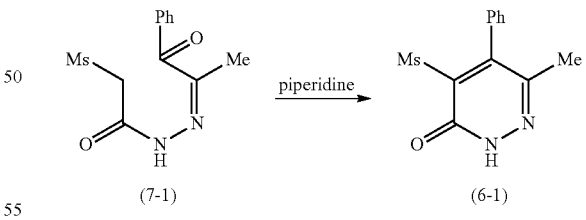

To a mixture of 4.6 mL of toluene and 564 mg of the compound (7-1), 85 mg of piperidine was added at room temperature under a nitrogen atmosphere. The mixture was stirred at 110° C. for 12 hours, and then cooled. Thereto, dilute hydrochloric acid was added, and then the mixture was extracted twice with ethyl acetate. The organic layers were combined, dried over anhydrous sodium sulfate, and then concentrated under reduced pressure. The resulting residue was subjected to silica gel column chromatography (elution solvent: hexane-ethyl acetate) to obtain 481 mg of the compound (6-1) (yield 91%).

Compound (6-1)

$^1$H-NMR (CDCl$_3$, TMS) δ (ppm): 2.04 (3H, s), 3.36 (3H, s), 7.18-7.21 (2H, m), 7.46-7.52 (3H, m), 11.61 (1H, br).

Reference Example 7

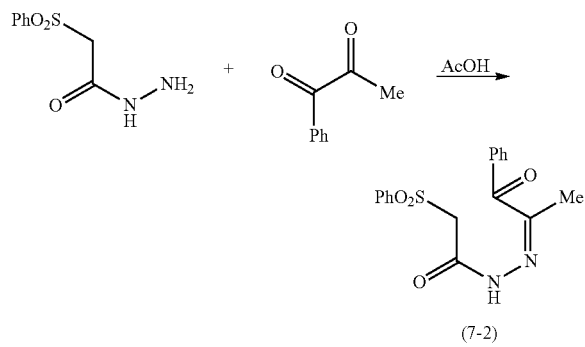

Experiment 1: A mixture of 321 mg of 2-phenylsulfonylacetic acid hydrazide, 206 mg of 1-phenylpropane-1,2-dione, 186 mg of acetic acid and 1.0 g of methanol was stirred at room temperature for 6 hours.

Experiment 2: A mixture of 322 mg of 2-phenylsulfonylacetic acid hydrazide, 201 mg of 1-phenylpropane-1,2-dione, 11 mg of acetic acid and 1.0 g of methanol was stirred at room temperature for 6 hours.

The reaction mixtures of Experiment 1 and Experiment 2 were combined, and the acetic acid was removed by toluene azeotrope (operations of adding toluene and concentrating the mixture under reduced pressure were carried out three times), and then the mixture was concentrated under reduced pressure to obtain 0.95 g (LC purity 88%) of 2-phenylsulfonylacetic acid 1-methyl-2-oxo-2-phenylethylidenehydrazide (hereinafter described as compound (7-2)). Yield: 89% including LC purity as the content.

Compound (7-2)

$^1$H-NMR (CDCl$_3$ TMS) δ: 8.95 (1H, s), 7.98 (2H, d, J=7.6 Hz), 7.82 (2H, d, J=7.8 Hz), 7.68-7.60 (2H, m), 7.51 (4H, td, J=7.5, 3.7 Hz), 4.48 (2H, s), 2.14 (3H, s).

Reference Example 8

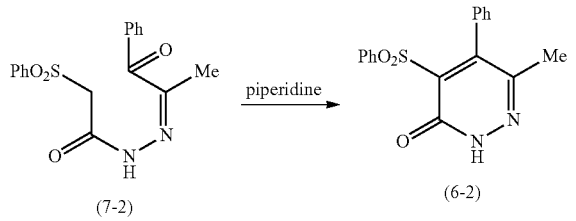

A mixture of 10 g of the compound (7-2), 2.7 g of piperidine and 31 g of toluene was stirred at 90° C. for 5 hours. The mixture was cooled to 40° C., 20 mL of water, and 20 mL of a 10% aqueous solution of sodium hydroxide, and 20 mL of toluene were added to separate the mixture. The organic layer was extracted with 20 mL of a 10% aqueous solution of sodium hydroxide, and the aqueous layer was combined, and then concentrated hydrochloric acid was added while stirring. The precipitated solid was collected by filtration, and the residue was sequentially washed with water and hexane, and dried under reduced pressure to obtain 9.35 g of the compound (6-2). Yield: 98%

Compound (6-2)

$^1$H-NMR (CDC$_3$ TMS) δ: 10.62 (1H, br s), 8.01-7.98 (2H, m), 7.61 (1H, t, J=7.5 Hz), 7.55-7.48 (5H, m), 7.24 (2H, dd, J=7.8, 1.8 Hz), 1.99 (3H, s).

Reference Example 9

The compound (1-1)(15 g) of toluene (35 g) solution was added to water (48 g) and was heated to 90° C. to remove toluene as an azeotropic mixture of water and toluene. After the complete removal of toluene, the slurry was filtered and the residue was washed with water and dried at 40° C. under reduced pressure. PXRD assay of the precipitated solids indicated phase-pure Form 1.

Reference Example 10

The compound (1-1) (15 g) of xylene (45 g) solution was heated to 100° C. to form a solution and n-heptane (30 g) was slowly added thereto at 100° C. The solution was cooled to 5° C. and was stirred for one hour. The slurry was filtered and washed with n-heptane in xylene (50 wt %). The precipitate was dried at 40° C. under reduced pressure. PXRD assay of the precipitated solids indicated phase-pure Form 1.

Reference Example 11

The compound (1-1) was combined with 5 times weight of methanol and mixed at 63° C. for 0.3 hour to form a solution. The solution was cooled to 10° C. and stirred for 1.5 hours. The slurry was filtered and washed with methanol. The precipitates were dried at 50° C. DSC/TGA and PXRD assay of the precipitated solids indicated phase-pure Form 1. FIGS. 1 and 2 are the charts of physical properties data of Form 1. The following table shows Peaks List of PXRD Pattern of Form 1.

| Pos. [°2 Th.] | Relative Intensity [%] |
| --- | --- |
| 11.9 | 47 |
| 13.1 | 86 |
| 13.7 | 100 |
| 15.3 | 31 |
| 18.0 | 41 |
| 18.5 | 32 |
| 19.7 | 55 |
| 22.2 | 41 |
| 22.7 | 100 |
| 23.0 | 68 |
| 24.0 | 40 |
| 24.9 | 48 |
| 27.3 | 36 |
| 32.5 | 27 |

Reference Example 12

The compound (1-1) (76.2 mg) was combined with 2 mL methanol in a 12 mL vial and mixed at 25° C. for 0.5 hour to form a solution. The solution was filtered through a 0.2 μm PTFE filter into a clean 12 mL vial. The vial was placed uncapped on top of a 50° C. metal block, and the solvent was allowed to evaporate for two days. DSC/TGA and PXRD assay of the precipitated solids indicated phase-pure Form 2.

FIGS. 3 and 4 are the charts of physical propeties data of Form 2. The following table shows Peaks List of PXRD Pattern of Form 2.

| Pos. [°2 Th.] | Relative Intensity [%] |
|---|---|
| 12.3 | 37 |
| 14.7 | 10 |
| 17.9 | 100 |
| 22.1 | 16 |
| 27.0 | 41 |

Reference Example 13

The compound (1-1) (260.6 mg) was combined with 8 mL methanol in a 12 mL vial and mixed at 25° C. for 0.5 hour to form a solution. The solution was filtered thru a 0.2 μm PTFE filter. A portion (~1 mL) of this solution was allowed to evaporate in a loosely-capped 12 mL vial for three days on top of a 50° C. metal block. DSC and PXRD assay of the precipitated solids indicated a new form, designated Form 3. FIGS. 5 and 6 are the charts of physical properties data of Form 3. The following table shows Peaks List of PXRD Pattern of Form 3.

| Pos. [°2 Th.] | Relative Intensity [%] |
|---|---|
| 10.5 | 100 |
| 21.1 | 16 |
| 31.8 | 15 |
| 31.9 | 6 |

FIG. 7 shows that solids Form 1 to 3 are different in PXRD pattern respectively.

Instrumentation:
Powder X-Ray Diffraction (PXRD). PXRD diffractograms were acquired using PANalytical X'Pert Pro diffractometer using Ni-filtered Cu Kα (45 kV/40 mA) radiation and a step size of 0.02° 2θ and X'celerator™ RTMS (Real Time Multi-Strip) detector.

Configuration on the incidental beam side, fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit. Samples were mounted flat on zero-background Si wafers.

Differential Scanning Calorimetry (DSC). DSC was conducted with a TA Instruments Q100 differential scanning calorimeter equipped with an autosampler and a refrigerated cooling system under 40 mL/min N2 purge. DSC thermograms were obtained at 15° C./min in crimped Al pans.
Thermogravimetric Analysis (TGA): TGA thermograms were obtained with a TA Instruments Q500 thermogravimetric analyzer under 40 mL/min N2 purge at 15° C./min in Pt or Al pans.

INDUSTRIAL APPLICABILITY

The pyridazine compound represented by the formula [1] useful as an active ingredient of a plant disease control agent can be produced, according to the method of the present invention.

The invention claimed is:
1. A method for producing a compound [1] comprising steps of;
obtaining a compound represented by formula [3]:

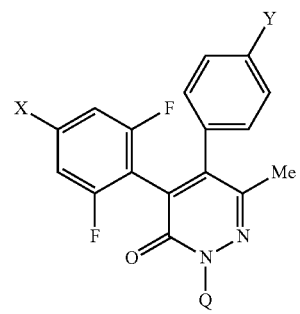

[3]

wherein Q represents an optionally halogenated C1 to C12 alkylsulfonyl group, a C6 to C24 arylsulfonyl group optionally substituted with at least one atom or group selected from group A, or a benzyl group in which at least one hydrogen atom on the benzene ring is optionally substituted with an atom or a group selected from group B,
X represents a hydrogen atom, a halogen atom or a methyl group, and
Y represents a hydrogen atom, a halogen atom or a methyl group,
by reacting a compound represented by formula [4]:

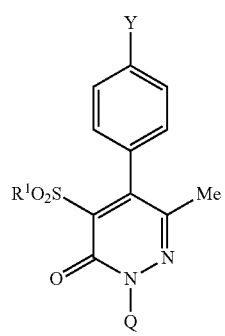

[4]

wherein $R^1$ represents an optionally halogenated C1 to C12 alkyl group, or represents a C6 to C24 aryl group optionally substituted with at least one atom or group selected from group A, and
Q and Y have the same meanings as described above,
Group A: a group consisting of optionally halogenated C1 to C4 alkoxy groups, halogen atoms and a nitro group,
Group B: a group consisting of optionally halogenated C1 to C4 alkyl groups, optionally halogenated C1 to C4 alkoxy groups, halogen atoms and a nitro group,
with a compound represented by formula [5]:

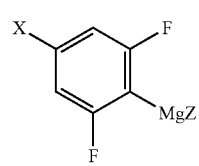

[5]

wherein X has the same meaning as described above, and Z represents a chlorine atom or bromine atom;

obtaining a compound represented by formula [2]:

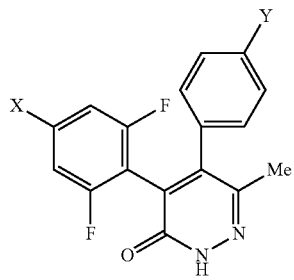

[2]

wherein X and Y have the same meanings as described above, by deprotecting the compound [3]; and obtaining a compound represented by formula [1]:

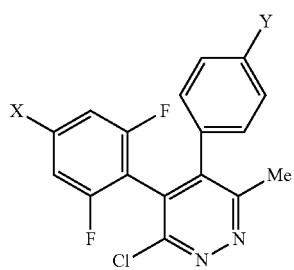

[1]

wherein X and Y have the same meanings as described above, by reacting the compound [2] with a chlorinating agent.

2. A method for producing a compound [1] comprising steps of;

obtaining a compound represented by formula [3]:

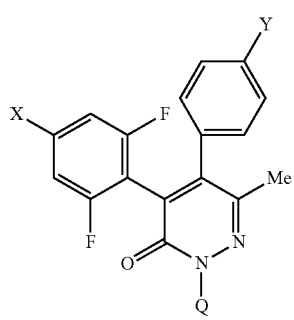

[3]

wherein Q represents an optionally halogenated C1 to C12 alkylsulfonyl group, a C6 to C24 arylsulfonyl group optionally substituted with at least one atom or group selected from group A, or a benzyl group in which at least one hydrogen atom on the benzene ring is optionally substituted with an atom or a group selected from group B, X represents a hydrogen atom, a halogen atom or a methyl group, and Y represents a hydrogen atom, a halogen atom or a methyl group, by reacting a compound represented by formula [4]:

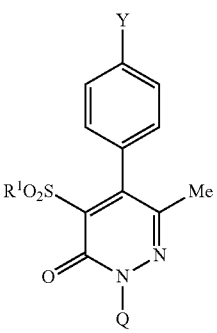

[4]

wherein $R^1$ represents an optionally halogenated C1 to C12 alkyl group, or represents a C6 to C24 aryl group optionally substituted with at least one atom or group selected from group A, and Q and Y have the same meanings as described above, Group A: a group consisting of optionally halogenated C1 to C4 alkoxy groups, halogen atoms and a nitro group, Group B: a group consisting of optionally halogenated C1 to C4 alkyl groups, optionally halogenated C1 to C4 alkoxy groups, halogen atoms and a nitro group, with a compound represented by formula [5]:

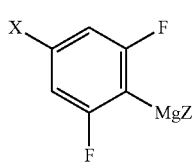

[5]

wherein X has the same meaning as described above, and Z represents a chlorine atom or bromine atom; and obtaining a compound represented by formula [1]

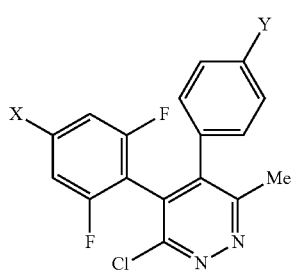

[1]

wherein X and Y have the same meanings as described above, by mixing the compound [3] with phosphorus oxychloride and heating the mixture.

3. A method for producing a compound [1] comprising steps of;

obtaining a compound represented by formula [3A]:

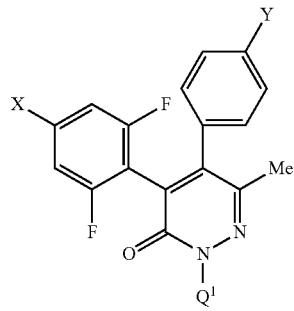

[3A]

wherein X represents a hydrogen atom, a halogen atom or a methyl group, Y represents a hydrogen atom, a halogen atom or a methyl group, and $Q^1$ represents an optionally halogenated C1 to C12 alkylsulfonyl group, or represents a C6 to C24 arylsulfonyl group optionally substituted with at least one atom or group selected from group A, Group A: a group consisting of optionally halogenated C1 to C4 alkoxy groups, halogen atoms and a nitro group, by reacting a compound represented by formula [4A]:

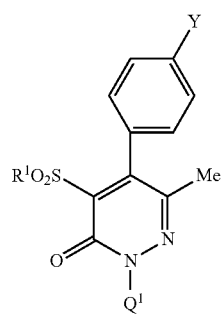

[4A]

wherein $R^1$ represents an optionally halogenated C1 to C12 alkyl group, or represents a C6 to C24 aryl group optionally substituted with at least one atom or group selected from group A, and wherein Y and $Q^1$ have the same meanings as described above, with a compound represented by formula [5]:

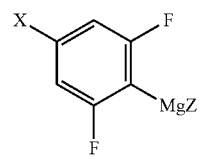

[5]

wherein X has the same meaning as described above, and Z represents a chlorine atom or bromine atom; and obtaining the compound [1]:

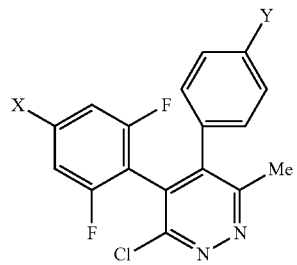

[1]

wherein X and Y have the same meanings as described above, by mixing the compound represented by formula [3A] with a secondary amine and then adding a chlorinating agent to the mixture.

4. A compound represented by formula [3]:

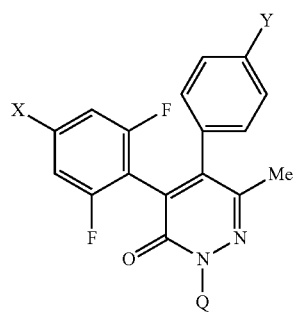

[3]

wherein Q represents an optionally halogenated C1 to C12 alkylsulfonyl group, a C6 to C24 arylsulfonyl group optionally substituted with at least one atom or group selected from group A, or a benzyl group in which at least one hydrogen atom on the benzene ring is optionally substituted with an atom or a group selected from group B, X represents a hydrogen atom, a halogen atom or a methyl group, and Y represents a hydrogen atom, a halogen atom or a methyl group, Group A: a group consisting of optionally halogenated C1 to C4 alkoxy groups, halogen atoms and a nitro group, Group B: a group consisting of optionally halogenated C1 to C4 alkyl groups, optionally halogenated C1 to C4 alkoxy groups, halogen atoms and a nitro group.

5. A method for producing a compound [3] represented by formula [3]:

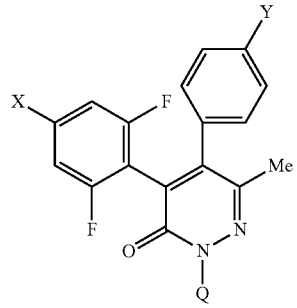

[3]

wherein Q represents an optionally halogenated C1 to C12 alkylsulfonyl group, a C6 to C24 arylsulfonyl group optionally substituted with at least one atom or group selected from group A, or a benzyl group in which at least one hydrogen atom on the benzene ring is optionally substituted with an atom or a group selected from group B, X represents a hydrogen atom, a halogen atom or a methyl group, and Y represents a hydrogen atom, a halogen atom or a methyl group, Group A: a group consisting of optionally halogenated C1 to C4 alkoxy groups, halogen atoms and a nitro group, Group B: a group consisting of optionally halogenated C1 to C4 alkyl groups, optionally halogenated C1 to C4 alkoxy groups, halogen atoms and a nitro group, by reacting a compound represented by formula [4]:

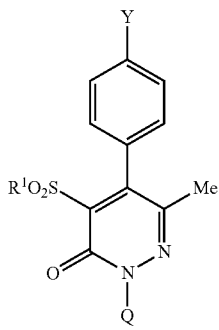

[4]

wherein $R^1$ represents an optionally halogenated C1 to C12 alkyl group, or represents a C6 to C24 aryl group optionally substituted with at least one atom or group selected from group A, and Q and Y have the same meanings as described above, with a compound represented by formula [5]:

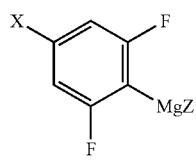

[5]

wherein X has the same meaning as described above, and Z represents a chlorine atom or bromine atom.

6. A compound represented by formula [4]:

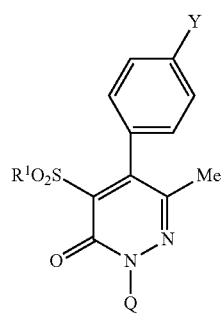

[4]

wherein $R^1$ represents an optionally halogenated C1 to C12 alkyl group, or represents a C6 to C24 aryl group optionally substituted with at least one atom or group selected from group A, and wherein Q represents an optionally halogenated C1 to C12 alkylsulfonyl group, a C6 to C24 arylsulfonyl group optionally substituted with at least one atom or group selected from group A, or a benzyl group in which at least one hydrogen atom on the benzene ring is optionally substituted with an atom or a group selected from group B, and Y represents a hydrogen atom, a halogen atom or a methyl group;

Group A: a group consisting of optionally halogenated C1 to C4 alkoxy groups, halogen atoms and a nitro group, and Group B: a group consisting of optionally halogenated C1 to C4 alkyl groups, optionally halogenated C1 to C4 alkoxy groups, halogen atoms and a nitro group.

* * * * *